(12) United States Patent
Ishihara et al.

(10) Patent No.: US 7,790,887 B2
(45) Date of Patent: Sep. 7, 2010

(54) MACROLIDE COMPOUND IN SOLID FORM, PROCESS FOR PREPARATION THEREOF, AND PHARMACEUTICAL COMPOSITION CONTAINING THE SAME

(75) Inventors: Hiroshi Ishihara, Ibaraki (JP); Manabu Sasho, Tokyo (JP); Keizo Sato, Ibaraki (JP); Takashi Kamahara, Chiba (JP); Masashi Yoshida, Tokyo (JP)

(73) Assignees: Eisai R&D Management Co., Ltd., Tokyo (JP); Mercian Corporation, Tokyo (JP)

( * ) Notice: Subject to any disclaimer, the term of this patent is extended or adjusted under 35 U.S.C. 154(b) by 127 days.

(21) Appl. No.: 12/021,184

(22) Filed: Jan. 28, 2008

(65) Prior Publication Data

US 2008/0214564 A1 Sep. 4, 2008

Related U.S. Application Data

(60) Provisional application No. 60/888,257, filed on Feb. 5, 2007.

(30) Foreign Application Priority Data

Jan. 29, 2007 (JP) ............................. 2007-017491

(51) Int. Cl.
*C07D 411/14* (2006.01)
(52) U.S. Cl. ....................................... 544/374; 544/229
(58) Field of Classification Search ................. 544/374
See application file for complete search history.

(56) References Cited

U.S. PATENT DOCUMENTS

| 5,977,109 | A | 11/1999 | Nakakura et al. |
| 6,712,617 | B2 | 3/2004 | Detmar et al. |
| 7,026,352 | B1 | 4/2006 | Mizui et al. |
| 7,256,178 | B2 | 8/2007 | Kotake et al. |
| 7,550,503 | B2 | 6/2009 | Kotake et al. |
| 7,576,204 | B2 | 8/2009 | Nagai et al. |
| 7,619,100 | B2 | 11/2009 | Kotake et al. |
| 7,667,052 | B2 | 2/2010 | Mizui et al. |
| 2003/0228404 | A1 | 12/2003 | Nishimoto et al. |
| 2006/0009439 | A1 | 1/2006 | Kotake et al. |
| 2006/0141589 | A1 | 6/2006 | Okuda et al. |
| 2006/0247203 | A1 | 11/2006 | Kato et al. |
| 2007/0155696 | A1 | 7/2007 | Ishihara et al. |
| 2008/0021226 | A1 | 1/2008 | Kanada et al. |
| 2008/0214564 | A1 | 9/2008 | Ishihara et al. |
| 2008/0255146 | A1 | 10/2008 | Kotake et al. |
| 2009/0325978 | A1 | 12/2009 | Onai et al. |

FOREIGN PATENT DOCUMENTS

| EP | 1083175 | A2 | 3/2001 |
| EP | 1508570 | A1 | 2/2005 |
| EP | 1880994 | A1 | 1/2008 |
| GB | 1153092 | A | 5/1969 |
| JP | 45-2754 | B | 1/1970 |
| JP | 54-103844 | A | 8/1979 |
| JP | 4-352783 | A | 12/1992 |
| JP | 10-502616 | A | 3/1998 |
| JP | 2001-348384 | A | 12/2001 |
| JP | 2002-145885 | A | 5/2002 |
| JP | 2004-269488 | A | 9/2004 |
| WO | WO 00/75126 | A1 | 12/2000 |
| WO | WO 02/12533 | A2 | 2/2002 |
| WO | WO 02/060890 | A1 | 8/2002 |
| WO | WO-03/099813 | A1 | 12/2003 |
| WO | WO 2004/098614 | A1 | 11/2004 |
| WO | WO 2005/073223 | A1 | 8/2005 |
| WO | WO-2005/116013 | A1 | 12/2005 |
| WO | WO 2006/075890 | A1 | 7/2006 |
| WO | WO-2006/121104 | A1 | 11/2006 |

OTHER PUBLICATIONS

Zell et. al. "Investigation of Polymorphism in Aspartame and Neotame Using Solid-State NMR Spectroscopy." Tetrahedron 2000, 56, 6603-6616.*
Morrisette "Elucidation of crystal form diversity of the HIV protease inhibitor ritonavir by high-throughput crystallization" Proceedings of the National Academy of Sciences 2003 100( 5) 2180-2184.*
Simone, Oncology: Introduction, Cecil Textbook of Medicine, 20th Edition, 1996 vol. 1, pp. 1004-1010.*
Trisha Gura "Cancer Models: Systems for Identifying New Drugs Are Often Faulty" Science Nov. 7, 1997: vol. 278. No. 5340, pp. 1041-1042.*
Zips et. al. "New Anticancer Agents: In Vitro and In Vivo Evaluation" in vivo 2005, 19, 1-7.*
Johnson, et. al. "Relationships between drug activity in NCI preclinical in vitro and in vivo models and early clinical trials." British Journal of Cancer 2001, 84, 1424-1431.*
International Preliminary Report on Patentability and Written Opinion of the International Searching Authority dated Aug. 4, 2009 for corresponding Application No. PCT/JP2008/051695.
Partial English language translation of WO-2005/116013-A1 (Dec. 8, 2005).
Partial English language translation of JP-2004-269488-A (Sep. 30, 2004).
Non-Final Office Action dated Sep. 15, 2009 of U.S. Appl. No. 10/532,412.
Notice of Allowance and Allowability dated Jun. 29, 2009 of U.S. Appl. No. 11/927,542.

(Continued)

*Primary Examiner*—Janet L Andres
*Assistant Examiner*—David K O'Dell
(74) *Attorney, Agent, or Firm*—Birch, Stewart, Kolasch & Birch, LLP

(57) ABSTRACT

The present invention provides the compound of formula (I) in a solid form which, as a bulk medicament for pharmaceutical manufacture, is uniform, has a high purity, and is easy to work with. The invention further provides a process for preparing this compound, and pharmaceutical compositions containing the same. A solid form of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide which has uniform specifications and is easy to work with was developed.

13 Claims, 7 Drawing Sheets

OTHER PUBLICATIONS

Notice of Allowance and Allowability dated May 18, 2008 of U.S. Appl. No. 11/213,962.
Ronald A. Lemahieu, et al., The Journal of Antibiotics, Jul. 1976, vol. 29, No. 7, pp. 728-734.
A. Anadon, Research in Veterinary Science, Jun. 1999, vol. 66, No. 3, pp. 197-203.
Akifumi, et al., "Shinkiko-shuyo kassei busshitsu pladienolide ni kansuru kenkyu (2) VEGF sansei yokusei kassei o shihyo to shita pladienolide-rui no kozo kassei sokan", Japan Society for Bioscience, Biotechnology, and Agrochemistry, Taikai Koen Yoshishu, Mar. 2003, p. 124.
Bestmann, Hans Jurgan, Synthesis, 1989, vol. 6, pp. 419-423.
Bestmann, Jans Jurgen, Angew. Chem. 1983, vol. 95, No. 10, pp. 810-811.
D.J. Farrell et al; Journal of Antimicrobial Chemotherapy, Sep. 2002, vol. 50, Suppl. pp. 39-47.
Eskens et al., "first-in-human clinical, pharmacokinetic (PK) and pharmacodynamic (PD) phase I study of the first-in-class spliceosome inhibito E7107 administered IV (bolus) on days 1, 8 and 15 every 28 days to patients with solid tumors", Abstract submission to: American Society of Clinical Oncology, date of submission: Jan. 6, 2009.
Final Office Action dated Mar. 4, 2009 of U.S. Appl. No. 10/532,412.
Furstner, Alois et al., Efficient Total Syntheses of Resin Glycosides and Analogues by Ring-Closing Olefin Methathesis, J. Am. Chem. Soc. 1999, vol. 121, pp. 7814-7821.
Gunawardana, Gaawanada, et al., J. Am. Chem. Soc. 1999, vol. 121, pp. 6092-6093.
Hamburg, Mats. Chem. Phys. Lipids, 1988, vol. 46, No. 4, pp. 253-243.
Hamberg, Mats. Lipids, 2000, vol. 35, No. 4, pp. 353-363.
Kazumi Sugimori, "the Sugimori C method," Seiyaku Koujou, vol. 6, No. 6, pp. 571-576, 1986.
Keiji et al., "Shinki ko-shuyo kassei busshitsu pladienolide ni kansuru kenkyu (3)-pladienolide-rui no yakuri kassei (in vitro, in vivo)", Japan Society for Bioscience, Biotechnology, and Agrochemistry, Taikai Koen Yoshishu, Mar. 2003, p. 124.
Kobayashi, Jun'ichi et al. Tetrahedron Letters, 1996, vol. 37, No. 9, pp. 1449-1450.
Moon-Seok Cha "Endogenous Production of Nitric Oxide by vascular Endothelial Growth Factor Down-Regulates Proliferation of Choriocarcinoma Cells", Biochemcial and Biophysical Research Communcations, vol. 282, pp. 1061-1066.
Non-Final Office Action dated Aug. 8, 2006 of U.S. Appl. No. 10/532,412.
Non-Final Office Action dated Feb. 11, 2009 for U.S. Appl. No. 11/927,542.
Non-Final Office Action dated Feb. 6, 2008 of U.S. Appl. No. 10/532,412.
Non-Final Office Action dated Jan. 9, 2006 of U.S. Appl. No. 10/515,647.
Non-Final Office Action dated Mar. 31, 2008 of U.S. Appl. No. 11/473,201.
Non-Final Office Action dated Oct. 9, 2008 of U.S. Appl. No. 11/213,962.
Notice of Allowance and Allowability dated Feb. 8, 2010 of U.S. Appl. No. 10/532,412.
Notice of Allowance and Allowability dated Feb. 3, 2009 of U.S. Appl. No. 11/473,201.
Notice of Allowance and Allowability dated Sep. 29, 2009 of U.S. Appl. No. 11/213,962.
Preliminary Amendment, Reply to Restriction Requirement and Election of Species dated Feb. 12, 2010 of U.S. Appl. No. 11/927,564.
Proceedings for 2003 Annual Meeting of Japan Society for Bioscience, Biotechnology and Agrochemistry, pp. 123-124, (2003).
Restriction Requirement dated Oct. 1, 2008 of U.S. Appl. No. 11/927,542.
Restriction Requirement dated Jun. 19, 2008 of U.S. Appl. No. 11/213,962.
Restriction Requirement dated Oct. 8, 2009 of U.S. Appl. No. 11/927,564.
Restriction Requirement dated Oct. 4, 2007 of U.S. Appl. No. 10/532,412.
Roberto Spagnoli, et al.: The Journal of Antibiotics, Apr. 1983, vol. 36, No. 4, pp. 365-375.
Rohr, Jurgen, Angew Chem Int. Ed., 2000, vol. 39, No. 16, pp. 2847-2849.
Ryuichi Morishita, "Recent Progress in Gene Therapy for Cardiovascular Disease", Circ Journal, vol. 66, pp. 1077-1086.
Sakai et al., "Shinki ko-shuyo kassei busshitsu pladienolide ni kansuru kenkyu (1)-shinki 12-inkan macrolide pladeienolide S no tanri to kozo", Japan Society for Bioscience, Biotechnology, and Agrochemistry, Taikai Koen Yoshishu, Mar. 2003, p. 123.
Seki-Asano, Mitsuko et al., "Isolation and Characterization of a New 12-Membered Macrolide FD-895," J. Antibiot., 1994, vol. 47, No. 12, pp. 1395 to 1401.
Supplemental Notice of Allowability dated Apr. 1, 2009 of U.S. Appl. No. 11/473,201.
Supplement Notice of Allowability dated Apr. 13, 2009 of U.S. Appl. No. 11/473,201.

* cited by examiner

US 7,790,887 B2

MACROLIDE COMPOUND IN SOLID FORM, PROCESS FOR PREPARATION THEREOF, AND PHARMACEUTICAL COMPOSITION CONTAINING THE SAME

This Nonprovisional application claims priority under 35 U.S.C. §119(e) on U.S. Provisional Application No. 60/888,257 filed on Feb. 5, 2007, and claims priority under 35 U.S.C. §119(a) on Patent Application No(s). 2007-17491 filed in Japan on Jan. 29, 2007, the entire contents of each of which are hereby incorporated by reference in their entirety.

TECHNICAL FIELD

The present invention relates to a macrolide compound in solid form, a process for preparation thereof, and pharmaceutical compositions containing the same. In particular, the invention relates to a macrolide compound in solid form which is useful as a medicament, a process for preparing the macrolide compound in solid form, and pharmaceutical compositions containing the same.

BACKGROUND ART

The macrolide compound of formula (I), below shown, (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide, as well as pharmaceutically acceptable salts and hydrates thereof, suppresses a vascular endothelial growth factor (VEGF) production, suppresses angiogenesis in cancer, and strongly suppresses solid tumor cell proliferation in in vivo experiments. Based on such effects, this compound has been reported to be particularly useful as a prophylactic or therapeutic agent for solid tumors and the like (see, for example, International Disclosure No. WO 03/099813).

General mention is made in WO 03/099813 that a series of 12-membered ring macrolide compounds and hydrates thereof are capable of forming crystal polymorphs. However, the compound of formula (I), which is the compound of Example 45 in WO 03/099813, is mentioned therein as being obtained as an oily substance; no disclosure whatsoever is made of the properties of a crystalline or amorphous solid form thereof. Nor has any disclosure been made of a process for preparing such a solid or of a pharmaceutical composition containing such a solid.

WO 03/099813 also discloses in detail a process for synthesizing the compound of formula (I). However, since post-treatment in this synthetic process is complex and purification by column chromatography is required in each step, there are aspects to the process that make it poorly conducive for the commercial production of a bulk medicament for pharmaceutical manufacture. Moreover, because the compound of formula (I) thus obtained has the properties of an oily substance, it has a poor uniformity and is of irregular purity, as a result of which it has not always been of sufficient quality for use as a bulk medicament for pharmaceutical manufacture.

In addition, the process described in WO 03/099813 requires the use of dichloromethane as the reaction solvent in synthesis of the compound of formula (I) and as the eluting solvent during column purification. Yet, dichloromethane, owing to its effects on the human body, is classed under UN Hazard Class 6.1 (Toxic Substances), and is categorized under the International Conference on Harmonization of Technical Requirements for Registration of Pharmaceuticals for Human Use (ICH) Quality Guideline Q3C (Impurities: Residual Solvents) as Class 2 (Solvents whose residual quantities in pharmaceutical products should be limited). Furthermore, in Japan, there are concerns over how this chemical is handled; for example, upper limit values for dichloromethane have been set as environmental standards for atmospheric pollution and water pollution.

DISCLOSURE OF THE INVENTION

It is therefore a purpose of the present invention to provide the compound of formula (I) in a solid form which, as a bulk medicament for pharmaceutical manufacture, is uniform, has a high purity, and is easy to work with. Further purposes of the invention are to provide a process for preparing this compound in solid form, and pharmaceutical compositions containing the same.

The inventors have conducted extensive investigations, as a result of which they have discovered that the solid form of the compound of formula (I) achieves the above purposes in terms of (1) a decreased level of impurities and (2) handling as a bulk medicament. Thus, they have accomplished the present invention.

Accordingly, the present invention provides the followings.

1) A solid form of the compound (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide represented by formula (I).

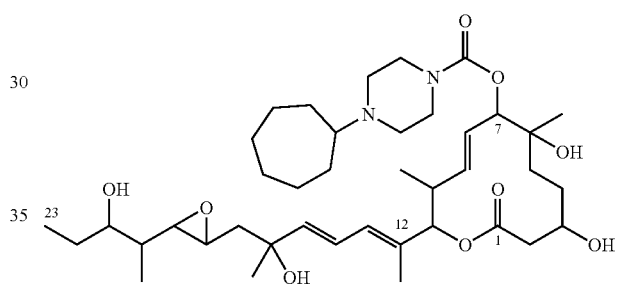

2) The solid of 1) above, wherein the solid form is crystalline.

3) The solid of 1) above, wherein the solid form is amorphous.

4) The solid of 2) above, wherein the crystals have, in a powder x-ray diffraction pattern thereof, peaks at the diffraction angles (2θ±0.2°) 8.8°, 15.8° and 17.5°.

5) A process for preparing the crystals of 2) or 4) above, including dissolving the (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide in one or two solvents selected from the group consisting of a first ether-type solvent, aromatic hydrocarbon-type solvents, acetate ester-type solvents and alkylnitrile-type solvents to form a solution; then adding an aliphatic hydrocarbon-type solvent to the solution so as to precipitate the crystals.

6) The preparation process of 5) above, wherein the one or two solvents selected from the group consisting of a first ether-type solvent, aromatic hydrocarbon-type solvents, acetate ester-type solvents and alkylnitrile-type solvents are an acetate ester-type solvent.

7) The preparation process of 5) or 6) above, wherein the acetate ester-type solvent is ethyl acetate.

8) The preparation process of any one of 5) to 7) above, wherein the aliphatic hydrocarbon-type solvent is n-heptane.

9) The preparation process of any one of 5) to 8) above, wherein the crystals are precipitated under stirring.

10) The process for preparing the crystals of any one of 5) to 9) above, wherein crystal precipitation is induced at 20 to 30° C.

11) The process for preparing the crystals of any one of 5) to 9) above, wherein crystal precipitation is induced at 35 to 60° C.

12) The process for preparing the crystals of any one of 5) to 9) above, wherein crystal precipitation is induced at 65 to 75° C.

13) The preparation process of 5) above, wherein the (8E, 12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide represented by formula (I) is prepared by the process including: reacting a compound represented by formula (VI):

(VI)

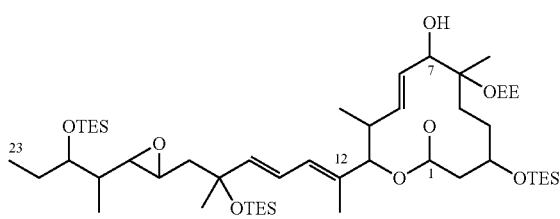

(wherein EE is a 1-ethoxyethyl group, and TES is a triethylsilyl group) with a compound represented by formula (VII):

(VII)

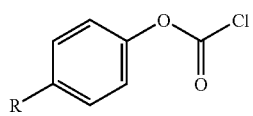

(wherein R is a nitro group, a chlorine atom or a hydrogen atom) using a second ether-type solvent so as to obtain an ether solution of the compound of formula (IV):

(IV)

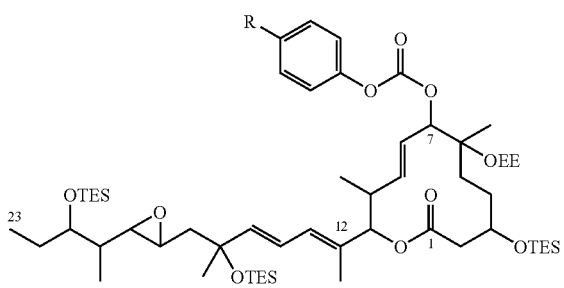

(wherein EE, TES and R are as defined above); reacting the ether solution of the compound of formula (IV) with 1-cycloheptylpiperazine so as to form an ether solution of the compound represented by formula (III):

(III)

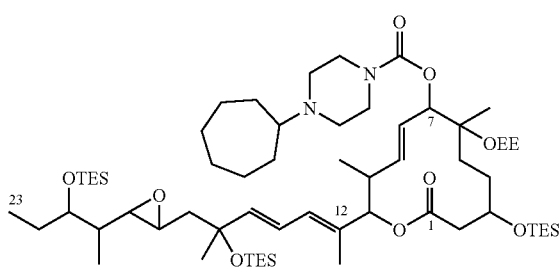

(wherein EE and TES are as defined above); treating the ether solution of the compound of formula (III) with a desilylating agent so as to deprotect the TES groups and thereby give an ether solution of the compound of formula (II):

(II)

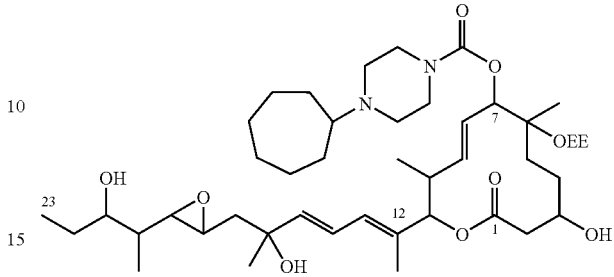

(wherein EE is as defined above); and treating the ether solution of the compound of formula (II) with an acid so as to deprotect the EE group.

14) The preparation process of 13) above, wherein the second ether-type solvent is t-butyl methyl ether.

15) A pharmaceutical composition comprising the solid of 1) above.

16) The pharmaceutical composition of 15) above, which is an anticancer agent.

17) Use of the solid compound of 1) above for manufacturing a pharmaceutical composition for treating cancer.

18) A method of treating cancer, comprising administering the solid of 1) above to a patient.

DETAILED DESCRIPTION OF THE INVENTION

Figure 1:
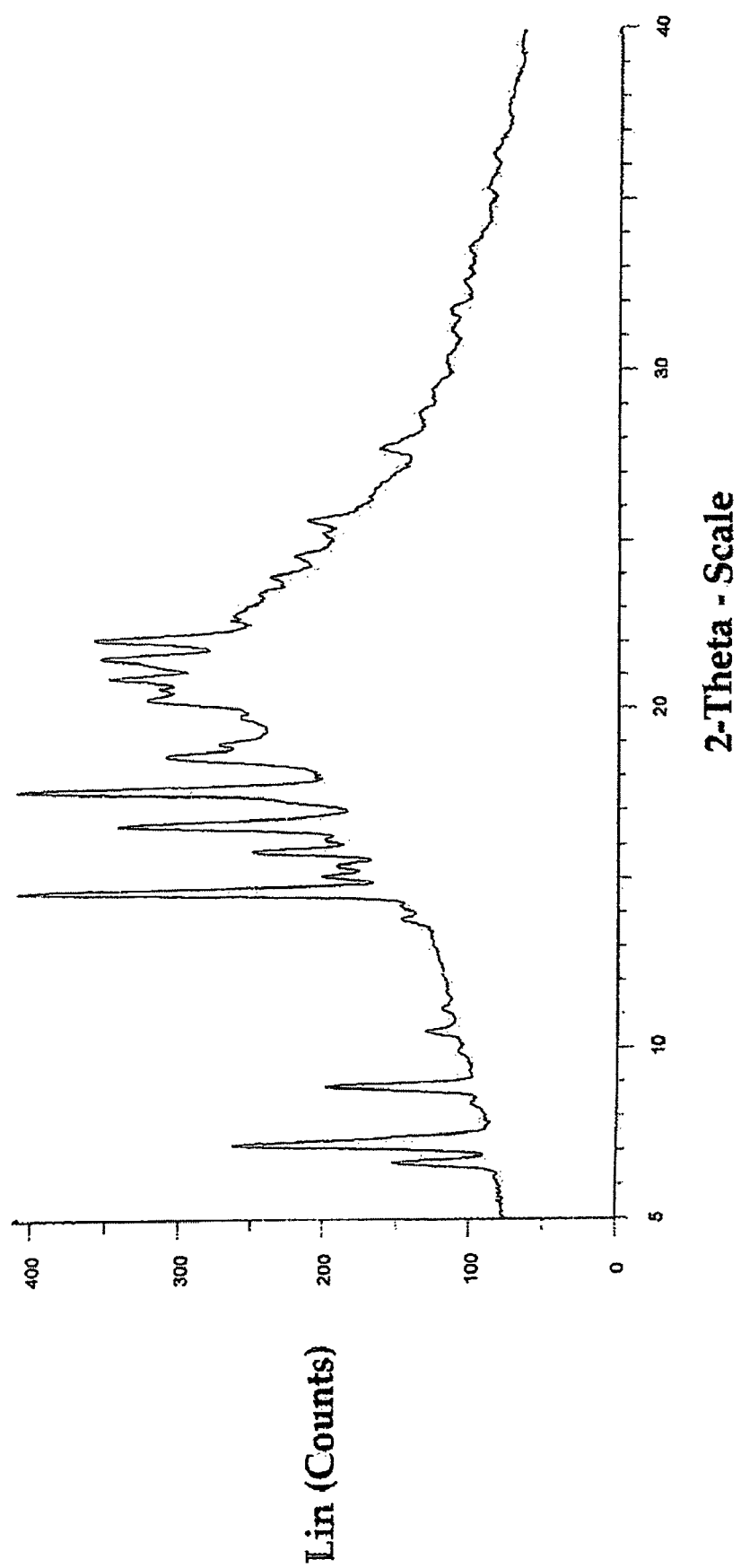
FIG. 1 shows a powder x-ray diffraction pattern for the crystals of formula (I) compound obtained in Example 7.

The solid form of the compound of formula (I) according to the present invention can suppress a vascular endothelial growth factor (VEGF) production, suppress angiogenesis in cancer, and is particularly useful as a medicament for the prevention or treatment of solid tumors and the like.

Embodiments of the invention are described below.

As used herein, "the solid form of the compound (8E,12E, 14E)-7-{(4-cycloheptylpiperazin-1-yl)carbonyl}oxy-3,6,16, 21-tetrahydroxy-6,10,12,16,20-pentamethyl-18,19-epoxytricosa-8,12,14-trien-11-olide" refers to the compound of formula (I) below, which is a macrolide compound having a 12-membered macrolactone ring as a partial structure, in a crystalline or amorphous form.

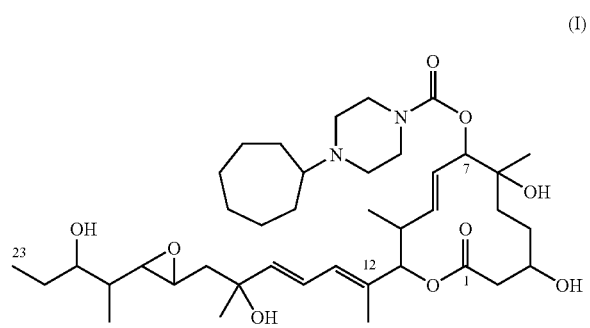

(I)

The solid form of the compound of formula (I) may be a non-solvate or a solvate. A "solvate of the compound of formula (I)" refers herein to a compound obtained by the salvation of solvent molecules in a non-solvate of the compound of formula (I). There is no particular limitation on the number of solvent molecules that are solvated.

In the present specification, the compound of formula (I) is shown, for the sake of convenience, as a planar chemical formula. However, certain isomers derived from the chemical formula may be included. That is, the present invention may include all isomers (e.g., geometric isomers, optical isomers based on asymmetric carbons, stereoisomers, and tautomers) which exist based on the structure of the compound, as well as isomeric mixtures. The isomer (3R,6R,7S,8E,10S,11S,12E,14E,16R,18R,19R,20R,21S)-7-[(4-cycloheptylpiperazin-1-yl)carbonyl]oxy-3,6,16,21-tetrahydroxy-6,10,12,16,20-pentamethyl-18,19-epoxytricosa-8,12,14-trien-11-olide shown in formula (I-a) below is especially preferred.

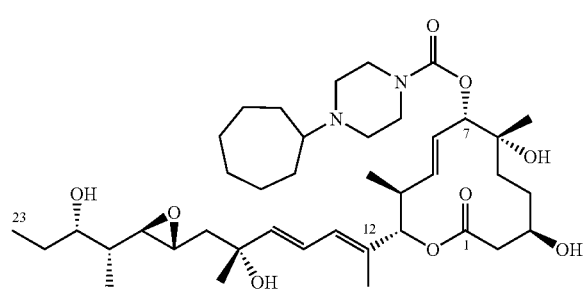

(I-a)

The powder x-ray diffraction analysis used in the present specification is an instrumental analysis technique employed for distinguishing between crystalline and amorphous substances and for crystal form identification. The diffraction peaks are typically measured using the Cu—Kα irradiation. The relative intensity of the respective diffraction peaks varies somewhat depending on the measurement conditions, the particle size of the measured sample and the crystal growth direction in the measured sample. Accordingly, the appeared pattern of diffraction peaks is important in confirming the identity of crystals. In the description that follows, the diffraction angles on the horizontal axis in the powder x-ray diffraction diagrams generally signify values that agree within a range of 2θ±0.2°.

Crystals of the compound of formula (I) have diffraction peaks at diffraction angles of 8.8° 15.8° and 17.5°, preferably have diffraction peaks at diffraction angles of 6.5°, 7.1°, 8.8°, 15.8° and 17.5°, and most preferably have diffraction peaks at diffraction angles of 6.5°, 7.1°, 8.8°, 14.6°, 15.8°, 16.5°, 17.5° and 22.0°. A "peak" here refers to a major peak having a relatively strong intensity. The invention encompasses crystals which have peaks of moderate intensity other than the above-indicated peaks.

More preferred crystals of the compound of formula (I) include crystals which have diffraction peaks at the same diffraction angles as in the powder x-ray diffraction diagram shown in FIG. 1, 3, 4, 6 or 7.

Amorphous forms of the compound of formula (I) include amorphous powders and amorphous masses. An amorphous powder is preferred.

As used in the present specification, "ether solution" refers to a solution obtained by treatment using an ether-type solvent.

Next, a process for preparing the solid form of the compound of formula (I) according to the invention is described in detail.

The solid form of formula (I) compound can be prepared by carrying out Step 1 to Step 6, as described below, and subsequently carrying out a crystal-forming step or an amorphous solid-forming step.

Synthetic Procedures

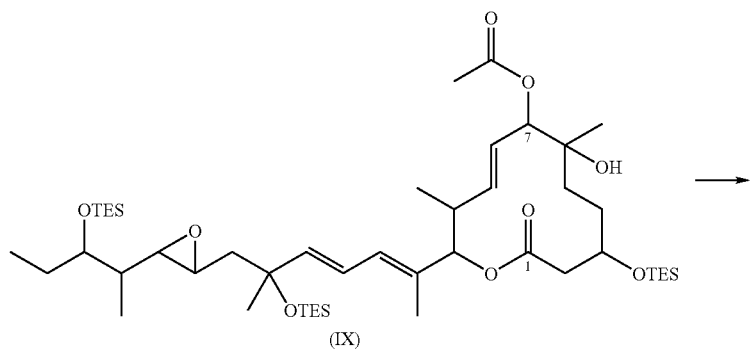

(IX)

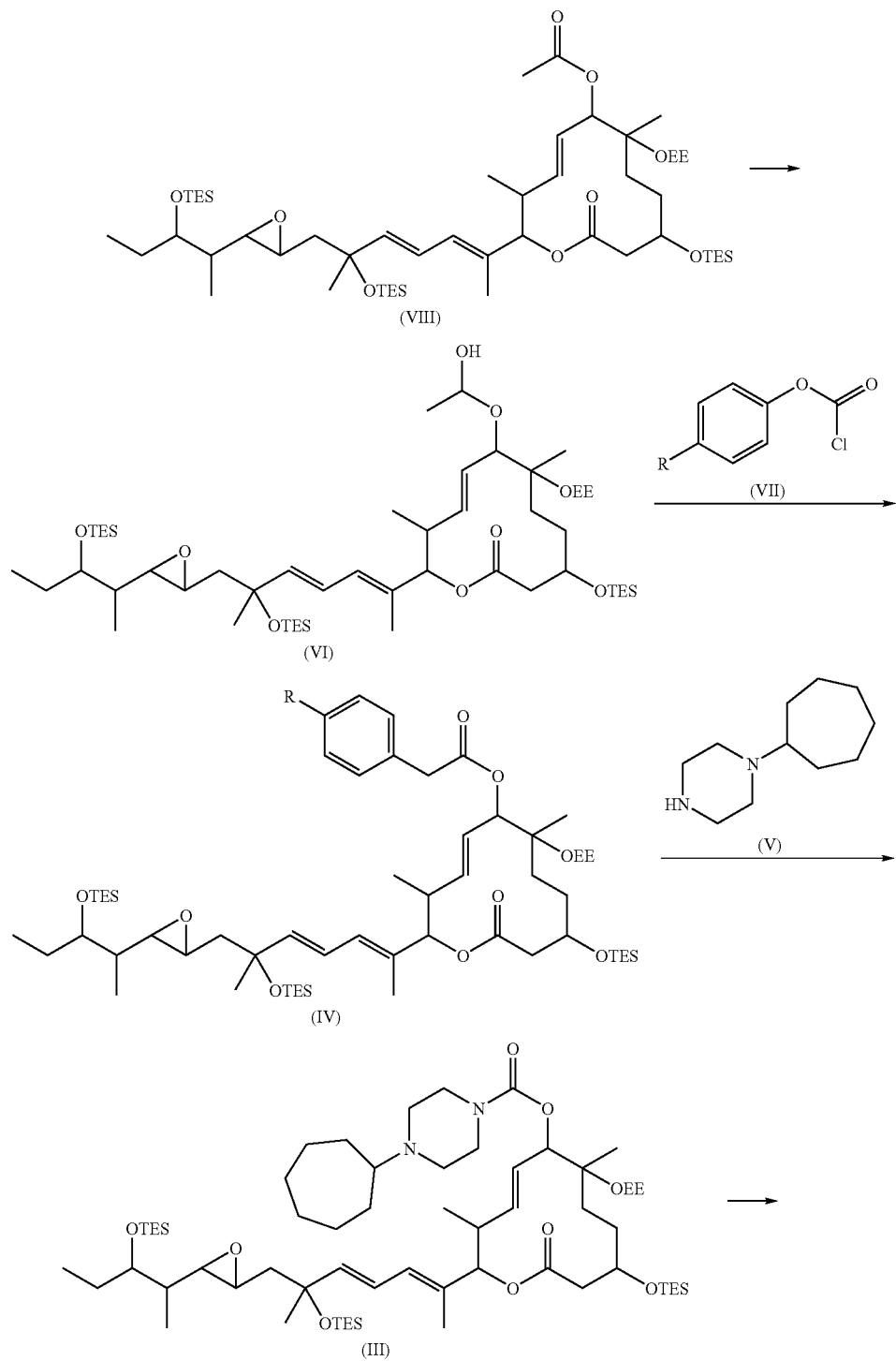

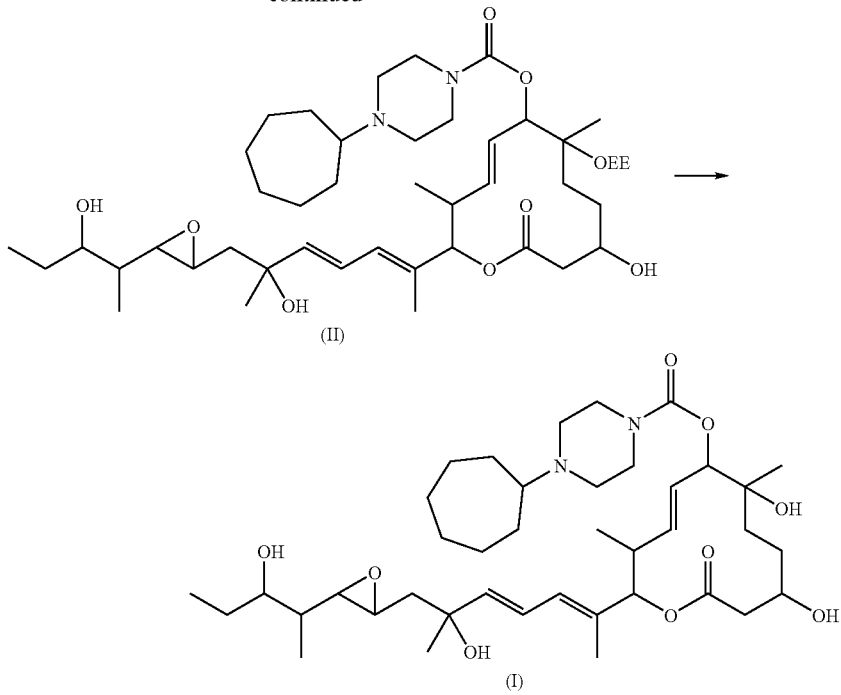

Step 1 of this preparation process is a step of reacting the compound of formula (IX) (wherein TES is a triethylsilyl group) with ethyl vinyl ether in the presence of an acid, thereby protecting the hydroxyl group at position 6 with 1-ethoxyethyl (EE) group to form the compound of formula (VIII). The solvent used in this step is not subject to any particular limitation, although an inert solvent which dissolves the starting materials to a certain degree but does not readily react with the starting materials is desirable. Illustrative examples include ether-type solvents such as tetrahydrofuran, diethyl ether, diisopropyl ether, t-butyl methyl ether, dioxane or 1,2-dimethoxyethane; hydrocarbon-type solvents such as hexane, benzene or toluene; ketone-type solvents such as acetone or methyl ethyl ketone; nitrile-type solvents such as acetonitrile; amide-type solvents such as N,N-dimethylformamide, N,N-dimethylacetamide, N-methyl-2-pyrrolidone or hexamethylphosphorylamide; sulfoxide-type solvents such as dimethylsulfoxide; and solvent mixtures thereof. Of the above, ether-type solvents such as tetrahydrofuran, diethyl ether, diisopropyl ether, t-butyl methyl ether, dioxane or dimethoxyethane; hydrocarbon-type solvents such as hexane, benzene or toluene; and solvent mixtures thereof are preferred.

The acid used in this step, while not subject to any particular limitation, may be an organic acid such as pyridinium p-toluenesulfonate, p-toluenesulfonic acid, camphorsulfonic acid, methanesulfonic acid or trifluoroacetic acid. The use of pyridinium p-toluenesulfonate, p-toluenesulfonic acid or camphorsulfonic acid is preferred.

The ethyl vinyl ether employed in this step may be used in anywhere from an equivalent amount to a large excess with respect to the compound of formula (IX).

However, in order to have the reaction proceed smoothly, the amount of ethyl vinyl ether used is preferably from 10 to 100 equivalents, and more preferably from 20 to 50 equivalents.

The acid may be used in anywhere from a catalytic amount to an equivalent amount with respect to the compound of formula (IX). An amount of from 0.005 to 0.50 equivalent is preferred, and an amount of from 0.005 to 0.20 equivalent is especially preferred.

The reaction time may be from 1 to 24 hours, and preferably from 2 to 10 hours. The reaction temperature is not subject to any particular limitation; the reaction will proceed around room temperature (24.0 to 26.0° C.).

Step 2 of this preparation process is a step of deprotect the compound of formula (VIII) at position 7 acetyl group to form the compound of formula (VI). Removal of the acetyl group may be carried out in accordance with a method described in the literature (see Protective Groups in Organic Synthesis, by T. W. Greene (John Wiley & Sons, 1981)), or a method that corresponds thereto, such as hydrolysis using an acid or base, or chemical reduction using a metal hydride complex. Preferred examples of the base include alkali metal hydroxides such as sodium hydroxide, potassium hydroxide or lithium hydroxide; alkali metal carbonates such as potassium carbonate, sodium carbonate, sodium bicarbonate or cesium carbonate; guanidine and guanidine nitrate. A mixed salt of guanidine and guanidine nitrate is especially preferred. The mixed salt of guanidine and guanidine nitrate may be used in an amount of from 1.0 to 2.0 equivalents, and preferably from 1.0 to 1.2 equivalents, with respect to the compound of formula (VIII). The solvent used in this step is not subject to any particular limitation, although an inert solvent which dissolves the starting materials to a certain degree but does not readily react with the starting materials is desirable. Illustrative examples include water; alcohol-based solvents such as methanol, ethanol, isopropanol or t-butanol; ether-based solvents such as tetrahydrofuran, diethyl ether, diisopropyl ether, dioxane or 1,2-dimethoxyethane; nitrile-type solvents such as acetonitrile; amide-type solvents such as N,N-dimethylformamide, N,N-dimethylacetamide, N-methyl-2-pyridone or hexamethylphosphorylamide; sulfoxide-type solvents such as dimethylsulfoxide; and solvent mixtures thereof. Of these, an alcohol-based solvent such as methanol or ethanol is preferred. The reaction temperature is not subject to any particular limitation, although a temperature of from 0 to 60° C. is preferred, a temperature of from 10 to 30° C. is more preferred, and a temperature of from 24.0 to 25.0° C. is even more preferred. The reaction may be carried out for a period of from 1 to 24 hours, and preferably from 3 to 10 hours.

Step 3 of this preparation process is a step of reacting the compound of formula (VI) with a compound of formula (VII) (p-nitrophenylchloroformate, p-chlorophenyl chloroformate or phenylchloroformate) in the presence of a base, to form a compound of formula (IV). The base used in this step is exemplified by aromatic bases such as pyridine, 4-dimethylaminopyridine, lutidine, collidine, imidazole or methylimidazole; tertiary alkylamines such as triethylamine or diisopropylethylamine; and inorganic bases such as potassium carbonate, sodium carbonate, cesium carbonate, sodium hydroxide or potassium hydroxide. Of these, triethylamine and 4-dimethylaminopyridine are preferred. It is desirable that the solvent used in this step be an inert solvent. For example, use may be made of ether-type solvents such as tetrahydrofuran, 1,2-dimethoxyethane, t-butyl methyl ether, cyclopentyl methyl ether, diethyl ether, diisopropyl ether, dibutyl ether or dicyclopentyl ether; aromatic hydrocarbon-type solvents such as benzene or toluene; aliphatic hydrocarbon-type solvents such as heptane or hexane; acetate ester-type solvents such as ethyl acetate, methyl acetate or isopropyl acetate; amide-type solvents such as N,N-dimethylformamide, N-methylpyrrolidone or N,N-dimethylacetamide; and sulfoxide-type solvents such as dimethylsulfoxide. Of these, t-butyl methyl ether and ethyl acetate are preferred.

The reaction temperature, which generally depends on the starting materials, solvent and other reagents used in the reaction, is preferably from 10 to 50° C., and more preferably from 24 to 28° C.

The reaction time generally depends on the starting materials, solvents and other reagents used in the reaction, and the reaction temperature. Typically, following addition of the reagents, the reaction mixture is stirred at the above-indicated reaction temperature for preferably from 1 to 24 hours, and more preferably from 4 to 10 hours.

Compound (VII) may be used in an amount of from 1.0 to 4.0 molar equivalents, and preferably from 2.0 to 3.0 molar equivalents, per mole of compound (VI).

4-Dimethylaminopyridine may be used in an amount of from 1.0 to 2.0 molar equivalents, and preferably from 1.1 to 1.3 molar equivalents, per mole of compound (VI). Triethylamine may be used in an amount of from 1.0 to 10.0 molar equivalents, and preferably from 4.0 to 6.0 molar equivalents, per mole of compound (VI).

Step 4 of this preparation process is a step of reacting 1-cycloheptylpiperazine with the compound of formula (IV), to form a compound of formula (III). It is desirable that the solvent used in this step, while not subject to any particular limitation, be an inert solvent which does not easily react with the starting materials. Illustrative examples of the solvent include alcohol-type solvents such as methanol, ethanol, isopropanol or t-butanol; ether-type solvents such as tetrahydrofuran, diethyl ether, diisopropyl ether, dioxane, dimethoxyethane, diethoxyethane, diglyme, t-butyl methyl ether, cyclopentyl methyl ether, dibutyl ether or dicyclopentyl ether; aliphatic hydrocarbon-type solvents such as hexane or heptane; aromatic hydrocarbon-type solvents such as benzene or toluene; ketone-type solvents such as acetone or methyl ethyl ketone; nitrile-type solvents such as acetonitrile; amide-type solvents such as N,N-dimethylformamide, N,N-dimethylacetamide, N-methyl-2-pyridine, N-methylpyrrolidone or hexamethylphosphorylamide; sulfoxide-type solvents such as dimethylsulfoxide; and acetate ester-type solvents such as ethyl acetate, methyl acetate or isopropyl acetate. Of these, ether-type solvents and acetate ester-type solvents are preferred. Diglyme, diethoxyethane, 1,2-dimethoxyethane, t-butyl methyl ether, ethyl acetate, and solvent mixtures thereof are more preferred. t-Butyl methyl ether and ethyl acetate are especially preferred.

The base used in this step is exemplified by the general organic bases and inorganic bases mentioned above. Illustrative examples include alkali metal alkoxides such as sodium methoxide, potassium t-butoxide or sodium t-butoxide; metal hydroxides such as sodium hydroxide or potassium hydroxide; aromatic bases such as pyridine, 4-dimethylaminopyridine, lutidine, collidine, imidazole or methylimidazole; tertiary alkylamines such as triethylamine or diisopropylethylamine; and alkali metal carbonates such as potassium carbonate, sodium carbonate or cesium carbonate. Of these, alkali metal alkoxides such as potassium t-butoxide; triethylamine and diisopropylethylamine are preferred.

1-Cyclobutylpiperazine may be used in an amount of from 1.0 to 3.0 molar equivalents, and preferably from 1.2 to 2.0 molar equivalents, per mole of compound (IV).

The reaction temperature, which generally depends on the starting materials, solvent and other reagents used in the reaction, is preferably from 10 to 50° C., and more preferably from 24 to 28° C.

The reaction time generally depends on the starting materials, solvents and other reagents used in the reaction, and the reaction temperature. Typically, following addition of the reagents, the reaction mixture is stirred at the above-indicated reaction temperature for preferably from 1 to 40 hours, and more preferably from 10 to 30 hours.

Step 5 of this preparation process is a step of deprotecting the compound of formula (III) at the 3, 16 and 21 positions triethylsilyl groups, to form the compound of formula (II). It is desirable that the solvent used in this step, while not subject to any particular limitation, be an inert solvent which does not easily react with the starting materials. Illustrative examples of the solvent include ether-type solvents such as tetrahydrofuran, t-butyl methyl ether, diethyl ether, diisopropyl ether, dioxane, 1,2-dimethoxyethane, cyclopentyl methyl ether, dibutyl ether or dicyclopentyl ether; aliphatic hydrocarbon-type solvents such as hexane or heptane; aromatic hydrocarbon-type solvents such as benzene or toluene; acetate ester-type solvents such as ethyl acetate, methyl acetate or isopropyl acetate; ketone-type solvents such as acetone or methyl ethyl ketone; nitrile-type solvent such as acetonitrile; amide-type solvents such as N,N-dimethylformamide, N,N-dimethylacetamide, N-methyl-2-pyridone, N-methylpyrrolidone, N,N-dimethylacetamide or hexamethylphosphorylamide; sulfoxide-type solvents such as dimethylsulfoxide; and solvent mixtures thereof. Of these, toluene, tetrahydrofuran, t-butyl methyl ether, and ethyl acetate are preferred. Ethyl acetate is especially preferred.

The desilylating agent used in this step is exemplified by tetrabutylammonium fluoride and hydrogen fluoride. The desilylating agent may be used in an amount of from 2.0 to 10.0 moles, and preferably from 3.0 to 8.0 moles, per mole of compound (III).

The reaction time is typically from 1 to 48 hours, and preferably from 15 to 30 hours. The reaction temperature is typically from 0 to 50° C., and preferably from 21.0 to 26.0° C.

Step 6 of this preparation process is a step of deprotecting the compound of formula (II) at the position 6 hydroxyl-protecting group, to form the compound of formula (I). Removal of the hydroxyl-protecting group may be carried out by, for example, solvolysis using an acid or a base. This reaction is preferably carried out using an inorganic acid such as sulfuric acid, hydrochloric acid or phosphoric acid; an organic sulfonic acid such as pyridinium p-toluenesulfonate, methanesulfonic acid, toluenesulfonic acid or camphorsulfonic acid; or an organic carboxylic acid such as trifluoroacetic acid or formic acid. The reaction is most preferably carried out using pyridinium p-toluenesulfonate. The acid may be used in anywhere from an equivalent amount to an excess with respect to the compound of formula (II). However, to have the reaction proceed smoothly and in view of other considerations such as purification treatment, the acid is preferably used in an amount of from 1.0 to 6.0 equivalents, and more preferably used in an amount of from 2.0 to 4.0 equivalents, with respect to formula (II) compound. The reaction time is typically from 1 to 24 hours, and preferably from 2 to 6 hours. The reaction temperature is typically from 0 to 50° C., and preferably from 21.0 to 27.0° C.

Steps 3 to 6 of this preparation process may be carried out as a series of successive operations without purification by column chromatography, thus enabling the compound of formula (I) to be efficiently prepared.

In such a case, the base used within the steps is exemplified by aromatic bases such as pyridine, 4-dimethylaminopyridine, lutidine, chollidine, imidazole or methylimidazole; tertiary alkylamines such as triethylamine or diisopropylethylamine; and inorganic bases such as potassium carbonate, sodium carbonate, cesium carbonate, sodium hydroxide or potassium hydroxide. Triethylamine and 4-dimethylaminopyridine are especially preferred. The solvent used within the steps is preferably an inert solvent, suitable examples of which include ether-type solvents (also referred to herein as "the second ether-type solvent") such as tetrahydrofuran, 1,2-dimethoxyethane, t-butyl methyl ether, cyclopentyl methyl ether, diethyl ether, diisopropyl ether, dibutyl ether or dicyclopentyl ether; aromatic hydrocarbon-type solvents such as benzene or toluene; aliphatic hydrocarbon-type solvents such as heptane or hexane; acetate ester-type solvents such as ethyl acetate, methyl acetate or isopropyl acetate; amide-type solvents such as N,N-dimethylformamide, N-methylpyrrolidone or N,N-dimethylacetamide; and sulfoxide-type solvents such as dimethylsulfoxide. t-Butyl methyl ether and ethyl acetate are especially preferred.

The crystal-forming step of this preparation process is a step of purifying the compound of formula (I) obtained in Step 6 above with column and dissolving the compound in a solvent, to prepare crystals of the compound of formula (I). Herein, the compound can be dissolved in a rich solvent at room temperature. After dissolved, the crystals may be precipitated by adding a poor solvent. Alternatively, the compound can be dissolved in a rich solvent under heating. After dissolved, the crystals may be precipitated either still under heating or by gradual cooling to room temperature and optionally by adding a poor solvent. Instead of formula (I) compound obtained in Step 6, use may be made of formula (I) compound obtained by the method described in Example 45 of WO 03/099813. Following addition of the poor solvent, it is preferable to continue stirring.

Illustrative examples of the rich solvent include acetate ester-type solvents such as ethyl acetate, methyl acetate or isopropyl acetate; ether-type solvents (also referred to below as the "first ether-type solvent") such as tetrahydrofuran, 1,2-dimethoxyethane, t-butyl methyl ether, cyclopentyl methyl ether, diethyl ether, diisopropyl ether, dibutyl ether or dicyclopentyl ether; aromatic hydrocarbon-type solvents such as toluene; and alkylnitrile-type solvents such as acetonitrile. Ethyl acetate is preferred.

Illustrative examples of the poor solvent include aliphatic hydrocarbon-type solvents such as n-heptane, n-hexane, n-pentane or cyclohexane. n-Heptane is preferred.

In one mode, no particular limitation is imposed on the amount of the solvents. It is preferable that the amount of the rich solvent is from 5 to 20 times, more preferably from 10 to 16 times, as much as the amount of the crude form of compound (I). It is preferable that the amount of the poor solvent is from 10 to 40 times, more preferably from 20 to 30 times, as much as the amount of the crude form of compound (I). The dissolution temperature is typically from 20 to 80° C., and preferably from 40 to 50° C. The crystallization temperature is typically from 15 to 40° C., and preferably in a near-room temperature range of from 20 to 30° C.

In another mode, no particular limitation is imposed on the amount of the solvents. It is preferable that the amount of the rich solvent is from 10 to 25 times, more preferably from 15 to 21 times, as much as the amount of the crude form of compound (I). It is preferable that the amount of the poor solvent is from 45 to 90 times, more preferably from 65 to 75 times, as much as the amount of the crude form of compound (I). The dissolution temperature is preferably from 20 to 80° C., and more preferably from 35 to 45° C. The crystallization temperature is preferably from 20 to 80° C., and more preferably from 65 to 75° C.

Further in another mode, no particular limitation is imposed on the amount of the solvents. It is preferable that the amount of the rich solvent is from 5 to 20 times, more preferably from 10 to 16 times, as much as the amount of the crude form of compound (I). It is preferable that the amount of the poor solvent is from 25 to 55 times, more preferably from 35 to 45 times, as much as the amount of the crude form of compound (I). The dissolution temperature is preferably from 20 to 80° C., and more preferably from 35 to 45° C. The crystallization temperature is from 20 to 80° C., and more preferably from 35 to 60° C.

It is also possible to prepare crystals of formula (I) compound by mixing together the above-mentioned rich solvent and poor solvent, dissolving compound (I) therein under heating, and then gradually cooling.

The step for forming amorphous solid in this preparation process is a step of dissolving the crystal obtained by the crystal-forming step (preferably, white crystals of formula (I) compound obtained by Example 7 to 9, 12 or 13) in water, or an appropriate organic solvent such as alcohols such as t-butanol or dimethyl sulfoxide, and subsequently freeze-drying the compound to prepare powder form of amorphous solid of the compound.

The freezing temperature is preferably −40° C. Preferred freeze-drying temperature and pressure conditions are as follows: after keeping at −20° C. and 10 Pa or below for about two hours, then maintain the pressure at 10 Pa or below with gradually raising the temperature to room temperature and, after about 14 hours, fill the system with nitrogen gas.

Instead, the amorphous solid-forming process in this preparation process may include a step in which, as another type of amorphous solid, an amorphous mass is formed.

This case may include a step of dissolving the crystals obtained in the above-described crystal-forming process (preferably white crystals of formula (I) compound obtained in the subsequently described Example 7) in ethyl acetate, and subsequently removing the solvent using a rotary evaporator, to form a clear, colorless amorphous mass.

(Powder X-Ray Diffraction Analysis)

Next, the powder x-ray diffraction patterns of the solid forms of formula (I) compound were measured.

(1) Measurement Method

The white crystals produced in Example 7 and the amorphous powder produced in Example 10, both of which are solid forms of formula (I) compound, were ground in an agate pestle, and measurement was carried out under the following conditions using a powder x-ray diffraction apparatus.

(2) Measurement Conditions

Measurement Method: transmission method
Apparatus: Discover D8 with GADDS, manufactured by Bruker AXS
Detector: two-dimensional PSCP
X-ray source: Cu 40 mA/40 kV
Sampling range: 0.01°
Operating range: 5 to 40°

(3) Results

Figure 2:
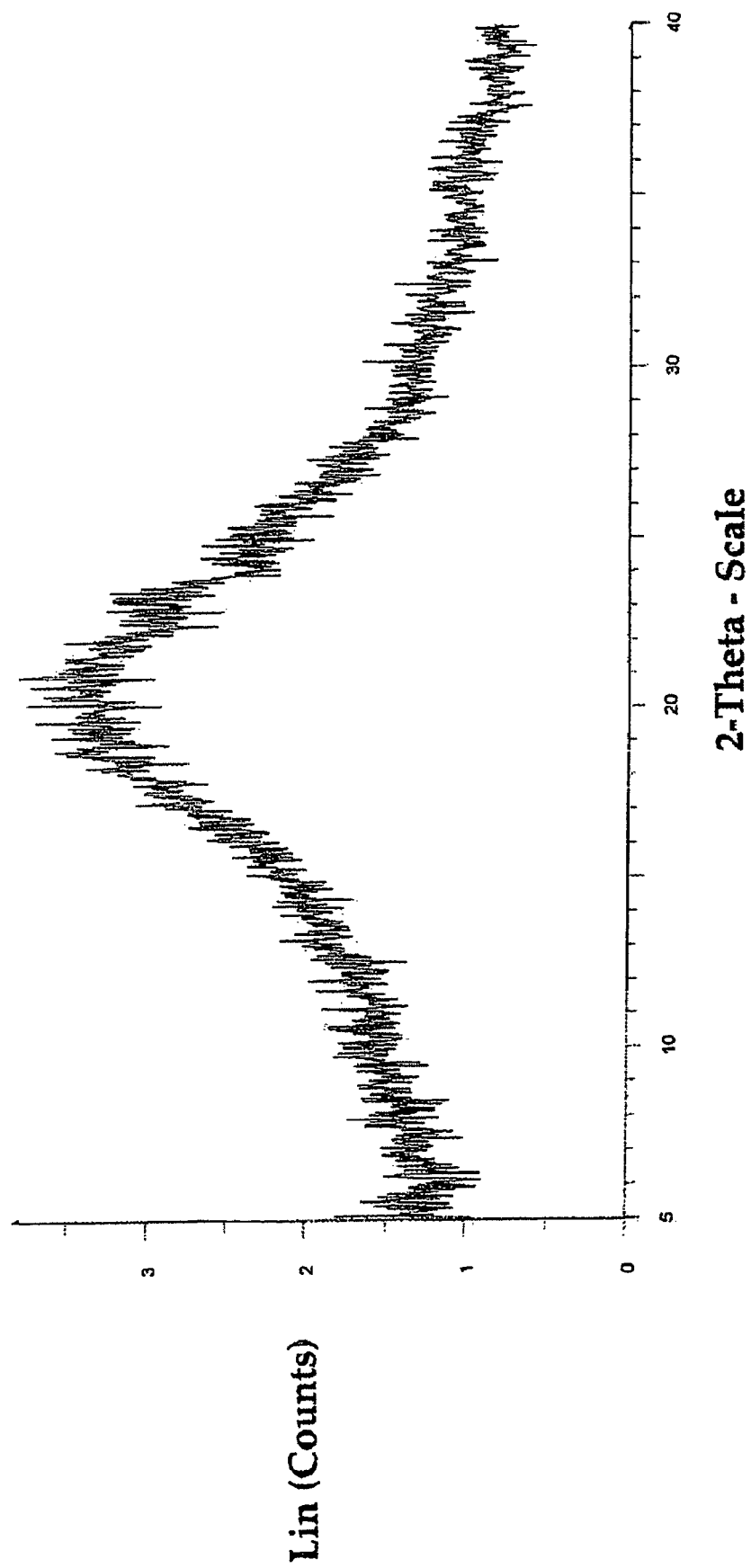
FIG. 2 shows a powder x-ray diffraction pattern for the amorphous powder of formula (I) compound obtained in Example 10.

FIG. 1 and Table 1 show the powder x-ray diffraction pattern for white crystals. FIG. 2 shows the powder x-ray diffraction pattern for an amorphous powder. Also, x-ray diffraction patterns for the white crystals obtained the alternative process were shown in FIGS. 3, 4, 6 and 7, and in Tables 5 to 8.

Typical diffraction angles in the powder x-ray diffraction pattern for the crystals are, as shown in Tables 1, 7 and 8, 8.8°, 15.8° and 17.5°; preferably 6.5°, 7.1°, 8.8°, 15.8° and 17.5°; and most preferably 6.5°, 7.1°, 8.8°, 14.6°, 15.8°, 16.5° 17.5° and 22.0°. As shown in FIG. 2, diffraction peaks were not observed in the powder x-ray diffraction pattern for the amorphous powder.

TABLE 1

| 2θ/θ values (°) of main peaks for white crystals |
| --- |
| 6.6 |
| 7.1 |
| 8.8 |
| 14.6 |
| 15.8 |
| 16.6 |
| 17.6 |
| 18.6 |
| 20.3 |
| 20.9 |
| 21.5 |
| 22.1 |

Then, the levels of impurities were measured by high-performance liquid chromatography (HPLC) so as to indicate the usefulness of the solid forms of formula (I) compound.

(1) Measurement Method

Samples of about 20 mg of the pale yellow amorphous solid and the white crystals of formula (I) compound, obtained in Example 7, were respectively dissolved in acetonitrile/water (v/v=7:3) to prepare respective solutions having a concentration of about 1 mg/mL. Using these solutions, HPLC analysis was carried out under the following measurement conditions.

(2) Measurement Conditions

Using the column and the mobile phases shown in Table 2 below, fluid was delivered for 60 minutes while varying the proportions of the mobile phase A and B liquids in such a way as to satisfy the gradient conditions shown in Table 3 below.

TABLE 2

| Column | X-Terra RP18 (4.6 mm I.D. 150 mm) |
| --- | --- |
| Mobile phase | Acetonitrile/water/sodium tetraborate mixture |
| | (solution A; v:v:w = 100:900:2) |
| | (solution B; v:v:w = 900:100:0) |
| Detection | UV 241 nm |
| Flow rate | 1.0 mL/min |
| Injected volume | 5 μL |
| Column temperature | 40° C. |

TABLE 3

| Fluid delivery time (min) | Concentration of solution B with respect to solution A (%) |
| --- | --- |
| 0 | 38 |
| 20 | 38 |
| 40 | 100 |
| 50 | 100 |
| 50.01 | 38 |
| 60 | 38 |

(3) Results

Based on the chromatographs obtained, the total impurities (%) in the pale yellow amorphous solid and the white crystals of formula (I) compound prepared in Example 7 were calculated according to the following equations (Eq. 1 and 2). Those results are shown in Table 4. When counting impurity peaks, those peaks having levels of 0.05% or below were handled so as not to be counted in Eq. 1 and 2.

Individual Impurity Amount (%)=peak area of each impurity÷(sum of peak areas for impurities+peak area of product)×100     (Eq. 1)

Total Impurity Amount (%)=Sum of individual impurity amounts     (Eq. 2)

TABLE 4

| Compound tested | Total impurity amount (%) |
| --- | --- |
| Pale yellow amorphous solid | 9.0 |
| White crystals | 2.9 |

As is apparent from the above results, the white crystals of formula (I) compound contain a lower level of impurities than the pale yellow amorphous solid, and thus have a good purity.

(Comparison of Solubility)

Next, the length of time required to dissolve about 1 mg/mL of the solid forms of formula (I) compound at room temperature in a pH 5.0 acetic acid buffer solution were measured.

(1) Measurement Method

After adding, at room temperature, a 25 mM potassium acetate buffer solution (pH 5.0) to, respectively, 10 mg of the white crystals prepared in Example 7, 10 mg of the amorphous powder prepared in Example 10, and 5 mg of the amorphous mass prepared in Example 11 in order to make a concentration of 5 mg/mL in each sample, the length of time required for complete dissolution under shaken at about 100 rpm was measured.

17

(2) Results

The times required for dissolution were as follows.
Crystals: about 32 seconds
Amorphous powder: about 10 seconds
Amorphous mass: about 215 seconds These results demonstrate that white crystals and an amorphous powder of formula (I) compound exhibit a higher solubility than an amorphous mass of the same compound.

The solid form of formula (I) compound according to the present invention is effective as a prophylatic/therapeutic medicament, by controlling gene expression, particularly against diseases for which a VEGF production-suppressing action is effective and against diseases for which an angiogenesis-suppressing action is effective.

In the present specification, "prophylatic/therapeutic" refers to prevention or treatment, or both prevention and treatment. More specifically, the solid form of formula (I) compound according to the present invention is effective as an anticancer agent, particularly as an anticancer agent/metastasis inhibitor for a solid tumor. The solid tumor is exemplified by pancreatic cancer, stomach cancer, colon cancer, breast cancer, prostate cancer, lung cancer, kidney cancer, brain tumors, cancers of the head and neck, esophageal cancer, skin cancer, liver cancer, uterine cancer, cervical cancer, bladder cancer, thyroid cancer, testicular tumors, chorionic cancer, osteosarcoma, soft tissue sarcoma and ovarian cancer. Cancers such as colon cancer, breast cancer, prostate cancer, lung cancer, cancers of the head and neck and ovarian cancer are especially preferred as the solid tumor. The solid form of formula (I) compound according to the present invention is also effective as an anticancer agent for leukemia, and is effective as well for the treatment of angioma. Moreover, based on the VEGF production-inhibiting action, the solid form of formula (I) compound according to the present invention is effective as a medicament for treating diabetic retinopathy, as a medicament for treating rheumatic arthritis and as a medicament for treating angioma. In addition, it is also an effective remedy for osteoarthritis, psoriasis, inflammatory disorders due to delayed hypersensitivity reactions, and medicaments for treating atherosclerosis.

When preparing the solid form of formula (I) compound according to the present invention as an injection, other ingredients such as pH adjustors, buffers, stabilizers and solubilizers may be optionally added to the active pharmaceutical ingredient, and the mixture can be prepared by a conventional method as a solution for subcutaneous, intramuscular, intraarticular or intravenous injection.

When the compound of the present invention is administered as a prophylactic/therapeutic medicament for various diseases, it may be administered orally as tablets, powders, granules, capsules, syrups or the like, or it may be administered parenterally as a spray, suppository, injection, external preparation or infusion. Although the dosage considerably depends on such factors as the severity of the symptoms, the age of the patient, and the type of disease, the compound can typically be administered from about 1 mg to about 100 mg per day to an adult, either once daily or as several divided doses each day.

The compound can be formulated by a conventional method using conventional pharmaceutical excipients. That is, when preparing a solid dosage form for oral administration, a filler is typically added to the active ingredient. Optionally, other additives such as binders, disintegrants, lubricants, colorants and correctives are also added, following which the material is rendered into tablets, coated tablets, granules, a powder, capsules or the like by a conventional method. Optionally, such tablets and granules may be provided with a sugar coating, a gelatin coating or some other suitable coating.

18

EXAMPLES

Examples are given below to more fully illustrate the present invention, although the examples provided here should not be construed as limiting the invention.

Abbreviations
EE: 1-ethoxyethyl group
TES: triethylsilyl group

Example 1

Preparation of (8E,12E,14E)-7-acetoxy-6-(1-ethoxyethoxy)-6,10,12,16,20-pentamethyl-3,16,21-tris(triethylsiloxy)-18,19-epoxytricosa-8,12,14-trien-11-olide

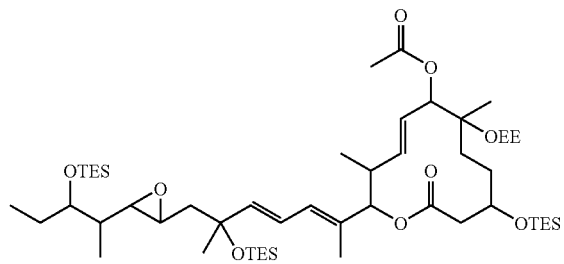

Under a nitrogen atmosphere and warming to hold the outside temperature at 25° C., 170 mL of tetrahydrofuran, 73 mL (759 mmol) of ethyl vinyl ether and 48 mg (0.19 mmol) of pyridinium p-toluenesulfonate were added to a toluene solution containing 17.0 g (19.0 mmol) of (8E,12E,14E)-7-acetoxy-6-hydroxy-6,10-12,16-20-pentamethyl-3,16,21-tris(triethylsiloxy)-18,19-epoxytricosa-8,12,14-trien-11-olide, following which stirring was carried out for 5 hours with maintaining the internal temperature at from 24.5 to 26.7° C. Next, 2.1 mL (15.2 mmol) of triethylamine was added to the reaction mixture and stirring was carried out for 5 minutes, following which 170 mL of t-butyl methyl ether and 170 mL of a 4% aqueous solution of sodium bicarbonate were added. The organic phase was separated, then washed with a 4% saline solution (170 mL) and subsequently dried over magnesium sulfate (17.0 g). After drying, the magnesium sulfate was removed by filtration, following which the filtrate was washed with t-butyl methyl ether (51 mL) then evaporated at 40° C., to give 22.9 g of a crude form (yellow oily substance) of the title compound.

Example 2

Preparation of (8E,12E,14E)-6-(1-ethoxyethoxy)-7-hydroxy-6,10,12,16,20-pentamethyl-3,16,21-tris(triethylsiloxy)-18,19-epoxytricosa-8,12,14-trien-11-olide

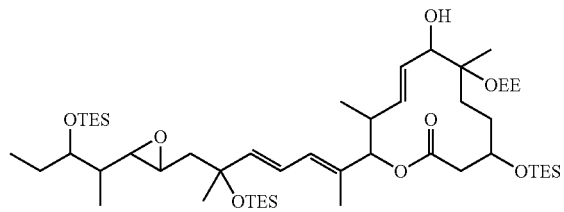

Under a nitrogen atmosphere and warming to hold the outside temperature at 25° C., 104 mL (20.8 mmol) of a 0.2 M solution of guanidine/guanidine nitrate in methanol was added to a methanol (79 mL) solution containing 18.4 g of (8E,12E,14E)-7-acetoxy-6-(1-ethoxyethoxy)-6,10,12,16, 20-pentamethyl-3,16,21-tris(triethylsiloxy)-18,19-epoxytricosa-8,12,14-trien-11-olide, following which stirring was carried out for 6 hours with maintaining the internal temperature at from 24.9 to 24.5° C. The reaction mixture was then ice-cooled and 276 mL of t-butyl methyl ether was added, following which 184 mL of a 10% aqueous solution of ammonium chloride was added. The organic phase was then separated, washed successively with water (184 mL) and a 4% saline solution (184 mL), and subsequently dried over magnesium sulfate (18.4 g). After drying, the magnesium sulfate was removed by filtration, following which the filtrate was washed with t-butyl methyl ether (55 mL) then evaporated at 40° C., yielding 19.7 g of a crude form (yellow oily substance) of the title compound (content: 73.4%; by weight, 14.5 g).

Example 3

Preparation of (8E,12E,14E)-6-(1-ethoxyethoxy)-6,10,12,16,20-pentamethyl-7-(4-nitrophenoxy)carboxy-3,16,21-tris(triethylsiloxy)-18,19-epoxytricosa-8,12,14-trien-11-olide

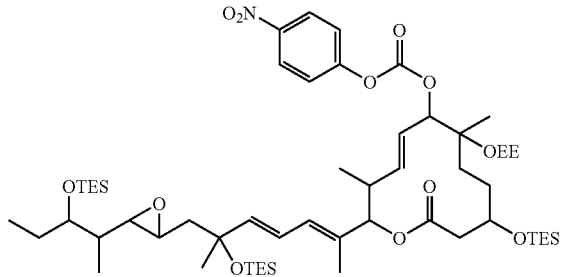

Under a nitrogen atmosphere and warming to hold the outside temperature at 25° C., 2.29 g (18.8 mmol) of 4-(dimethylamino)pyridine, 10.9 mL (78.2 mmol) of triethylamine and 8.13 g (39.1 mmol) of p-nitrophenyl chloroformate were added to a t-butyl methyl ether (217 mL) solution of 14.5 g (15.6 mmol) of (8E,12E,14E)-6-(1-ethoxyethoxy)-7-hydroxy-6,10,12,16,20-pentamethyl-3,16,21-tris(triethylsiloxy)-18,19-epoxytricosa-8,12,14-trien-11-olide, following which stirring was carried out for 7 hours 30 minutes with maintaining the external temperature at 25° C. Water (145 mL) was then added to the reaction mixture, after which the organic phase was separated, yielding a t-butyl methyl ether solution of the title compound.

Example 4

Preparation of (8E,12E,14E)-7-{(4-cycloheptylpiperazin-1-yl)carbonyl}oxy-6-(1-ethoxyethoxy)-6,10,12,16,20-pentamethyl-3,16,21-tris(triethylsiloxy)-18,19-epoxytricosa-8,12,14-trien-11-olide

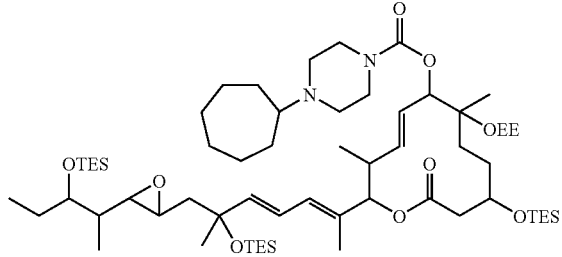

Under a nitrogen atmosphere and warming to hold the outside temperature at 25° C., a t-butyl methyl ether solution (29 mL) of 4.28 g (23.5 mmol) of 1-cycloheptylpiperazine was added dropwise over a period of 2 minutes to a t-butyl methyl ether solution of the (8E,12E,14E)-6-(1-ethoxyethoxy)-6,10,12,16,20-pentamethyl-7-(4-nitrophenoxy)carboxy-3,16,21-tris(triethylsiloxy)-18,19-epoxytricosa-8,12,14-trien-11-olide obtained in Example 3. The reaction mixture was then stirred for 17 hours while being held at an outside temperature of 25° C. Next, 145 mL of a 10% aqueous solution of ammonium chloride was added to the reaction mixture and the organic phase was separated, then successively washed with 145 mL of a 4% aqueous solution of sodium bicarbonate and 145 mL of water, yielding a t-butyl methyl ether solution of the title compound.

Example 5

Preparation of (8E,12E,14E)-7-{(4-cycloheptylpiperazin-1-yl)carbonyl}oxy-6-(1-ethoxyethoxy)-3,16,21-trihydroxy-6,10,12,16,20-pentamethyl-18,19-epoxytricosa-8,12,14-trien-11-olide

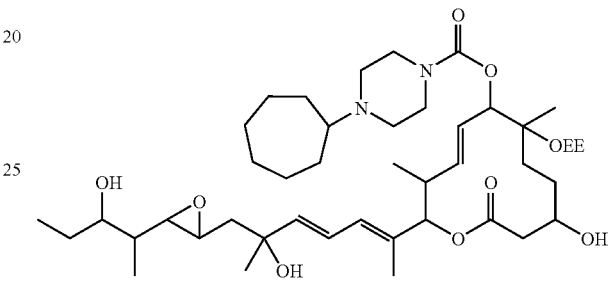

Under a nitrogen atmosphere and warming to hold the outside temperature at 25° C., tetrahydrofuran (145 mL) was added to a t-butyl methyl ether solution of the (8E,12E,14E)-7-{(4-cycloheptylpiperazin-1-yl)carbonyl}oxy-6-(1-ethoxyethoxy)-6,10,12,16,20-pentamethyl-3,16,21-tris(triethylsiloxy)-18,19-epoxytricosa-8,12,14-trien-11-olide obtained in Example 4, following which 93.8 mL (93.8 mmol) of a 1.0 M tetrahydrofuran solution of tetrabutylammonium fluoride was added dropwise over a period of 3 minutes. The reaction mixture was then stirred for 22 hours while being held at room temperature (25° C.). Water (145 mL) was added to this reaction mixture and the organic phase was separated, then washed with water (145 mL), yielding a t-butyl methyl ether/tetrahydrofuran solution of the title compound.

Example 6

Preparation of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide

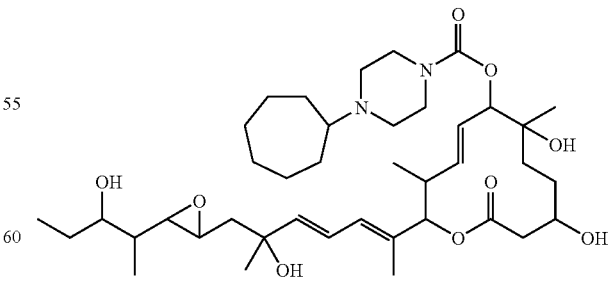

At an outside temperature of 25° C., tetrahydrofuran (145 mL) and t-butanol (62.1 mL) were added to a t-butyl methyl ether/tetrahydrofuran solution of the (8E,12E,14E)-7-{(4-cycloheptylpiperazin-1-yl)carbonyl}oxy-6-(1-ethoxyethoxy)-3,16,21-trihydroxy-6,10,12,16,20-pentamethyl-18,19-epoxytricosa-8,12,14-trien-11-olide obtained in Example 5, following which 11.8 g (46.9 mmol) of pyridinium p-toluenesulfonate was added and stirring was carried out for 3 hours. Next, t-butyl methyl ether (104 mL) and a saturated aqueous solution of sodium bicarbonate (104 mL) were added to the reaction mixture, following which the organic phase was separated and washed with a 4% saline solution (104 mL), then evaporated, yielding 50.6 g (content: 20.2%; by weight, 10.2 g) of a crude form (yellow oily substance) of the title compound.

Example 7

Preparation of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide in solid form First, 34.7 g (content, 9.60 g) of the compound obtained by solvent distillation from 47.8 g of the crude form of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 6 was dissolved in ethyl acetate (40 mL) and filtered. Next, heptane (8 mL) was added and purification was carried out using silica gel column chromatography (the eluting solvents were, in order: 1) ethyl acetate/heptane=50:50; 2) ethyl acetate/heptane=80:20; 3) ethyl acetate; and 4) methanol/ethyl acetate=3:97). The purified fractions were collected and evaporated, giving 13.5 g of the title compound (content, 9.02 g) as a pale yellow amorphous solid.

Using a 45° C. water bath and an ultrasonic cleaner, 13.5 g (content, 9.02 g) of the above pale yellow amorphous solid was dissolved in ethyl acetate (99 mL) and the resulting solution was filtered (with glass wool filter paper, and using 18 mL of ethyl acetate to wash the solution onto the filter paper), following which n-heptane (117 mL) was added dropwise over a period of 6 minutes at room temperature. After 30 minutes, 117 mL of n-heptane was further added dropwise over a period of 30 minutes, then stirring was carried out for 19 hours 30 minutes at 23° C. and 98 rpm. Next, using a stirrer (BL600, manufactured by Heidon Co. Ltd.), stirring was carried out for 35 minutes at 183 rpm, after which the aggregated precipitates were broken up with a spatula, and stirring was carried out for another 22 hours 30 minutes. The crystals were filtered within an isolator, then washed with n-heptane/ethyl acetate (2:1, 65 mL). The crystals thus obtained were dried in vacuo at room temperature (23° C.) for 23 hours, giving 8.44 g (content: 97.6%; by weight, 8.24 g) of the title compound as white crystals. FIG. 1 shows the powder x-ray diffraction pattern for the white crystals obtained. The x-ray diffraction patterns were measured under the above-mentioned conditions.

The $^1$H-NMR (400 MHz, CD$_3$OD) spectrum of the compound thus obtained agreed with the values shown in Example 45 of WO 03/099813.

Example 8

Preparation of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide crystals (Alternative Process 1)

Figure 3:
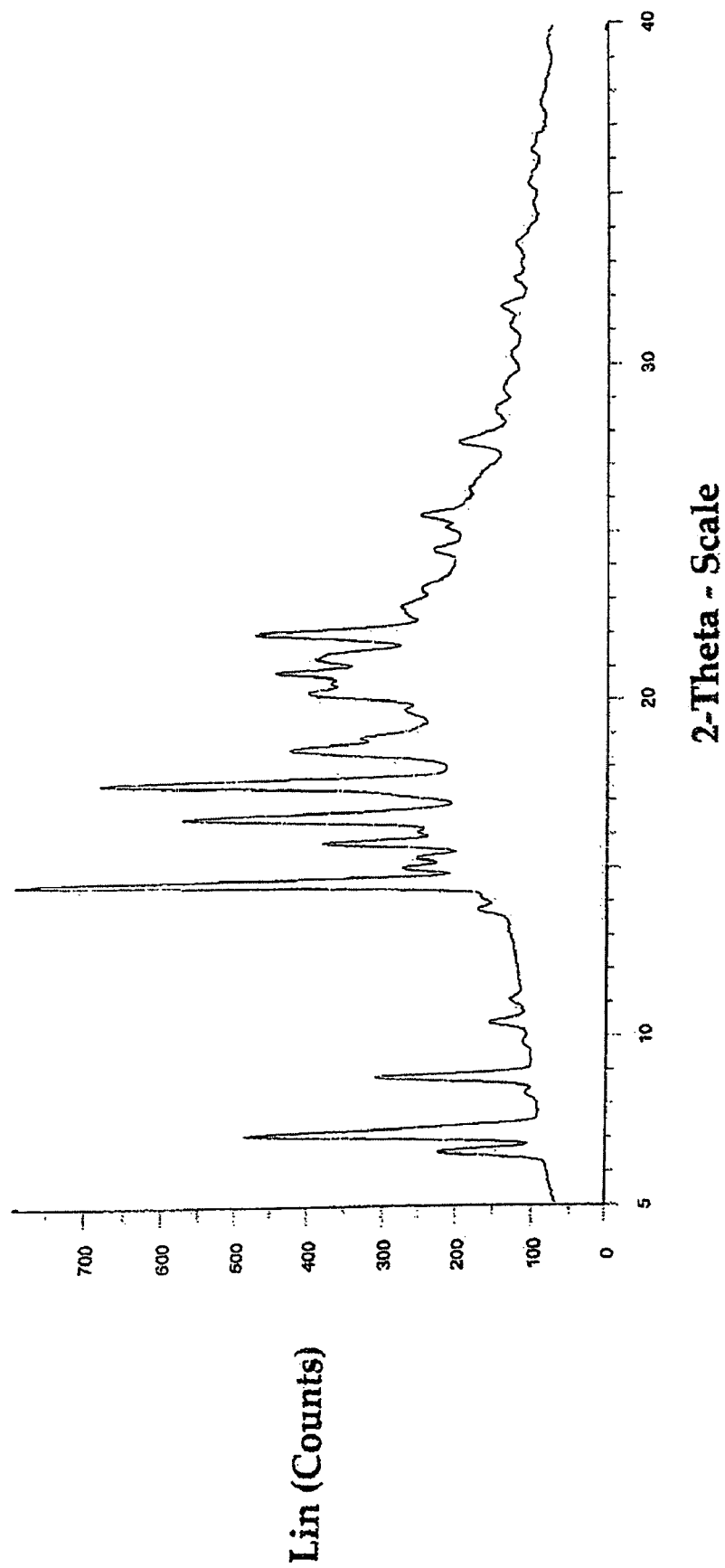
FIG. 3 shows a powder x-ray diffraction pattern for the crystals of formula (I) compound obtained in Example 8.

First, about 100 mg of the pale yellow amorphous solid of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 7 was completely dissolved in 1 mL of ethyl acetate, and 3 mL of n-heptane was added thereto. After confirming the appearance of a white solid in the solution, the solution was placed on a hot plate at approximately 80° C. and the white solid was completely dissolved. The solution was left to stand again at room temperature and thereby cooled, following which the resulting suspension was filtered using filter paper, thereby obtaining white crystals. The powder x-ray diffraction pattern for the resulting white crystals is shown in FIG. 3, and the typical peak values are shown in Table 5. This product had diffraction peaks at the same diffraction angles as in the powder x-ray diffraction pattern shown in FIG. 1. The x-ray diffraction patterns were measured in the same manner as Example 7.

TABLE 5

| 2θ/θ values (°) of main peaks for white crystals |
|---|
| 6.5 |
| 7.1 |
| 8.8 |
| 14.6 |
| 15.8 |
| 16.6 |
| 17.5 |
| 18.5 |
| 20.2 |
| 20.9 |
| 21.3 |
| 22.0 |

Example 9

Preparation of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide crystals (Alternative Process 2)

Figure 4:
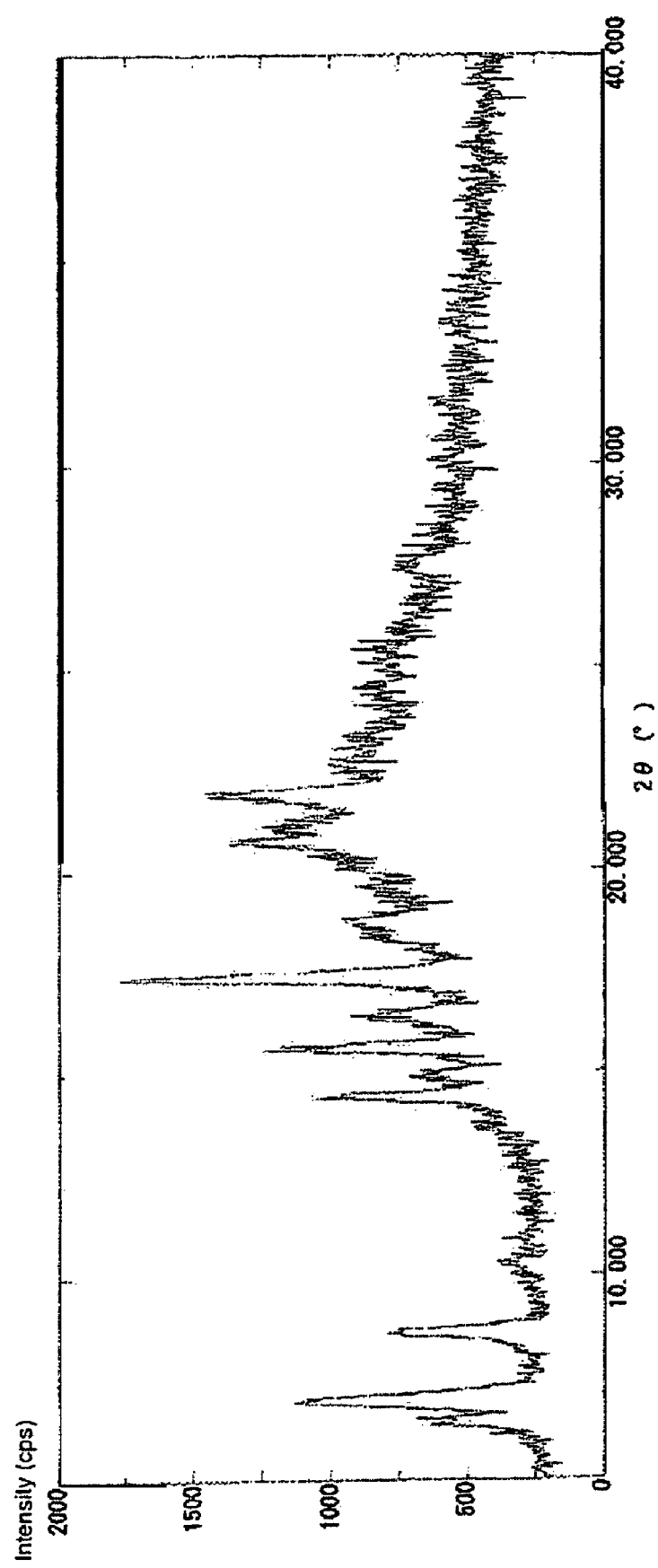
FIG. 4 shows a powder x-ray diffraction pattern for the crystals of formula (I) compound obtained in Example 9.

First, 200 mg of the pale yellow amorphous solid of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 7 was completely dissolved in 20 mL of a solvent mixture of water and t-butanol (water/t-butanol=1:1 (v/v)), and 1 mL portions of the resulting solution were placed in 5 mL glass vials. The vials were frozen at −40° C. using a freeze dryer, then maintained at a shelf temperature of −20° C. and a pressure of 10 Pa or below for about 2 hours, following which the shelf temperature was gradually raised to room temperature with maintaining the pressure at 10 Pa or below. After about 14 hours, the vials were filled with nitrogen gas, thereby giving glass vials containing a white powder. Next, 0.1 mL of acetonitrile was added per vial and the white powder at the interior was completely dissolved, following which the vials were stored for about 17 hours in a refrigerator set to about 5° C. The solid that formed within these vials was removed and left to stand at room temperature, thereby giving white crystals. The powder x-ray diffraction pattern for the resulting white crystals is shown in FIG. 4, and the typical peak values are shown in Table 6. This product had diffraction peaks at the same diffraction angles as in the powder x-ray diffraction pattern shown in FIG. 1. The x-ray diffraction patterns were measured under the following conditions using a powder x-ray diffraction apparatus.

(Measurement Method)
   Measurement Method: reflection method
   Apparatus: MiniFlex, manufactured by Rigaku Corporation
   Detector: one-dimensional scintillation counter
   X-ray source: Cu 15 mA/30 kV
   Sampling range: 0.01°
   Operating range: 5 to 40°

TABLE 6

| 2θ/θ values (°) of main peaks for white crystals |
| --- |
| 6.5 |
| 7.0 |
| 8.7 |
| 14.4 |
| 15.6 |
| 16.6 |
| 17.4 |
| 18.8 |
| 22.0 |

Example 10

Preparation of an amorphous solid of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide by freeze-drying First, 148 mg of the white crystals of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 7 was completely dissolved in 36 mL of a solvent mixture of water and t-butanol (water/t-butanol=1:1 (v/v)), and 2 mL portions of the resulting solution were placed in 5 mL glass vials. The vials were frozen at −40° C. using a freeze dryer, then maintained at −20° C. and a pressure of 10 Pa or below for about 2 hours, following which the temperature was gradually raised to room temperature with maintaining the pressure at 10 Pa or below. After about 14 hours, the vials were filled with nitrogen gas, thereby giving a white amorphous powder. The powder x-ray diffraction pattern for the resulting amorphous powder is shown in FIG. 2. The x-ray diffraction patterns were measured in the same manner as Example 7.

Example 11

Figure 5:
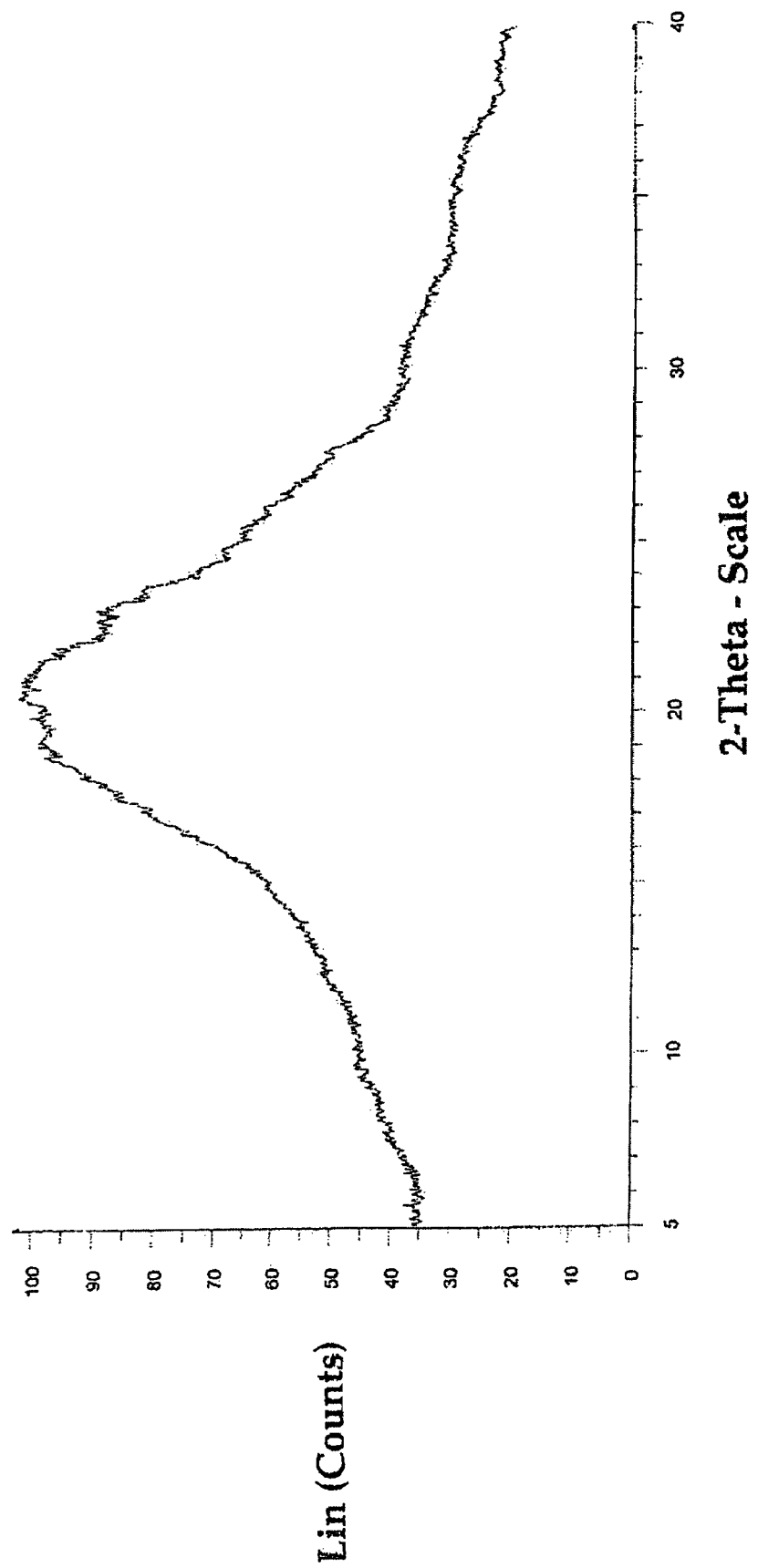
FIG. 5 shows a powder x-ray diffraction pattern for the amorphous mass of formula (I) compound obtained in Example 11.

Preparation of an amorphous solid of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide by evaporation First, 66 mg of the white crystals of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 7 was completely dissolved in 12 mL of ethyl acetate, and 1 mL portions of the resulting solution were poured into glass Spitz tubes. The solvent was removed from the tubes using a rotary evaporator, thereby giving clear, colorless amorphous masses. FIG. 5 shows the powder x-ray diffraction pattern for the resulting amorphous mass. The x-ray diffraction patterns were measured in the same manner as Example 7.

Example 12

Preparation of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide crystals ((Alternative Process 3) at 70° C.)

Figure 6:
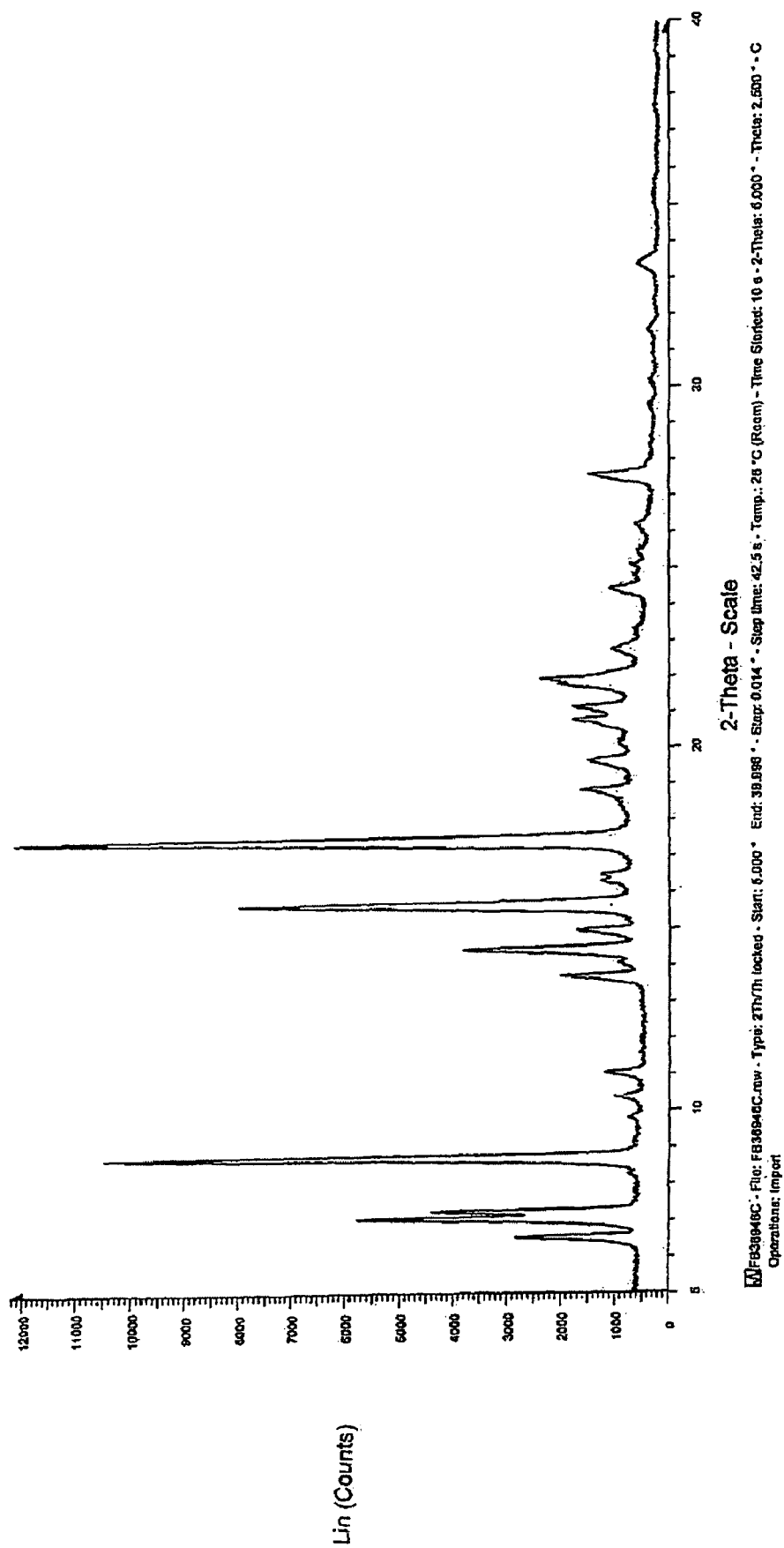
FIG. 6 shows a powder x-ray diffraction pattern for the crystals of formula (I) compound obtained in Example 12.

To 5.20 g (content 2.75 g) of the amorphous solid of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 7 was added 27.5 mL of ethyl acetate. The mixture was heated to 40° C., to be completely dissolved. Then, the solution was filtered at room temperature (using PTFE filter paper, washed with 22.5 mL of ethyl acetate). The filtrate was heated to 40° C. and 50 mL of n-heptane was added thereto. The mixture was further heated to 70° C. and, 85.1 mL of n-heptane was added thereto with keeping the temperature. The seed crystals were added to the solution, followed by stirring at 70° C. for 2 hours. Then, 64.9 mL of n-heptane was added thereto over 2.1 hour with keeping the temperature, followed by stirring at 70° C. for 1 hour. The obtained suspension was filtered using filter paper, thereby obtaining crystals, and then washed with n-heptane:ethyl acetate (3:1, 27.5 mL). The obtained crystals were dried under vacuum at room temperature for 16.5 hours, to give 2.44 g of white crystals. The crystals obtained in Example 7 were used as the seed crystals. The powder x-ray diffraction pattern for the obtained white crystals is shown in FIG. 6, and the typical peak values are shown in Table 7. The x-ray diffraction patterns were measured under the following conditions using a powder x-ray diffraction apparatus.

(Measurement Condition)
  Measurement Method: reflection method
  Apparatus: Discover D8 Advance, manufactured by Bruker AXS
  Detector: one-dimensional high speed PSD
  X-ray source: Cu 40 mA/35 kV
  Sampling range: 0.01°
  Operating range: 5 to 40°

TABLE 7

| 2θ/θ values (°) of main peaks for white crystals |
| --- |
| 6.5 |
| 7.2 |
| 8.7 |
| 14.4 |
| 15.7 |
| 16.3 |
| 17.5 |
| 20.8 |
| 21.9 |

Example 13

Preparation of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide crystals ((Alternative Process 4) at 55° C. to 40° C.)

Figure 7:
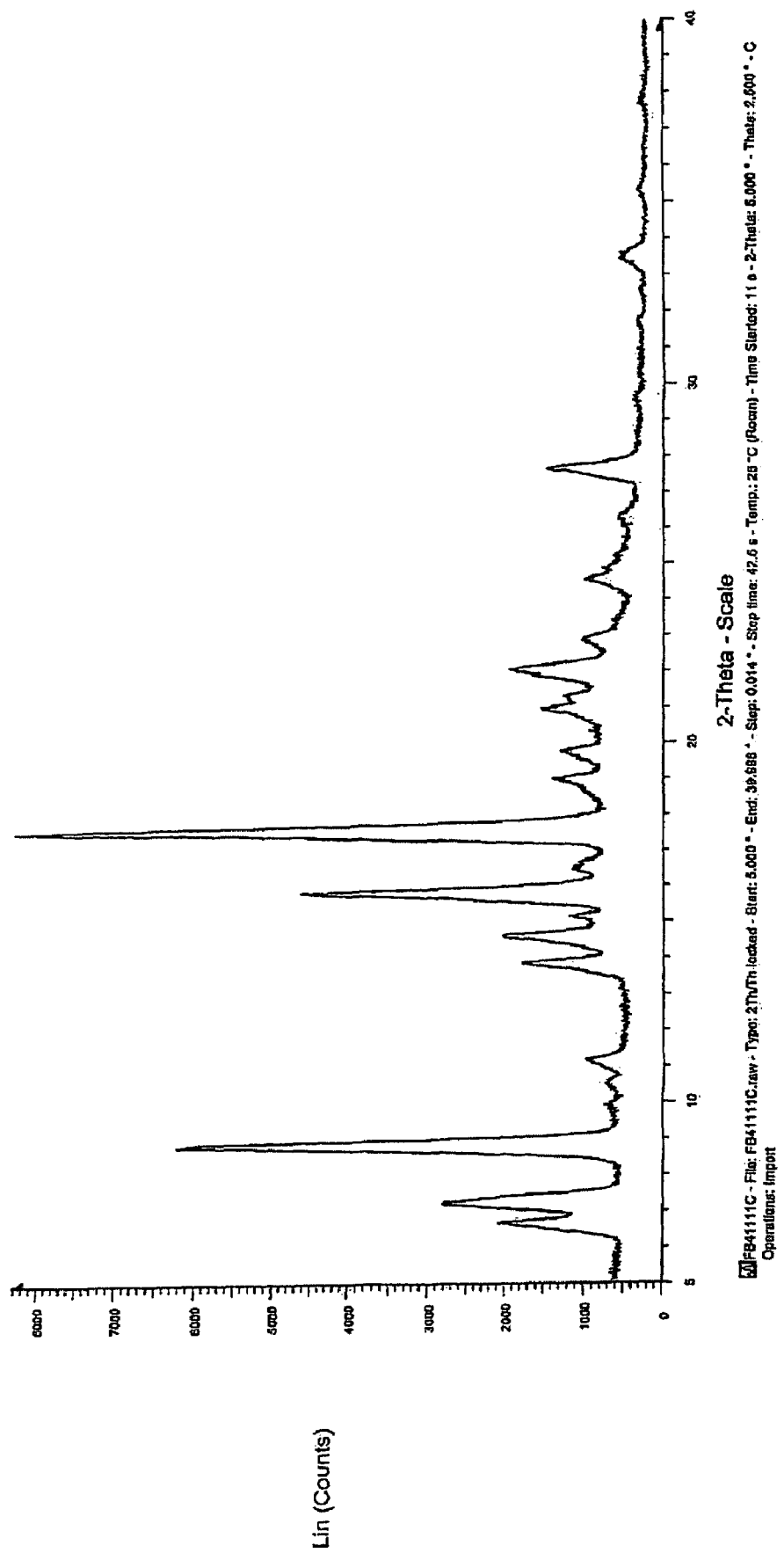
FIG. 7 shows a powder x-ray diffraction patter for the crystals of formula (I) compound obtained in Example 13.

To 1.90 g (content 1.71 g) of the amorphous solid of (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide obtained in Example 7 was added 15 mL of ethyl acetate. The mixture was heated to 40° C., to be completely dissolved. Then, the solution was filtered at room temperature (using PTFE filter paper, washed with 7 mL of ethyl acetate). The filtrate was heated to 40° C. and 22 mL of n-heptane was added thereto. The mixture was further heated to 55° C. and, 11 mL of n-heptane was added thereto with keeping the temperature. The seed crystals were added to the solution, followed by stirring for 1.5 hours. Then, 33 mL of n-heptane was added thereto over about 1 hour with keeping the temperature, followed by cooling as it was gradually to 40° C. The obtained suspension was filtered using filter paper, thereby obtaining crystals, and then washed with n-heptane:ethyl acetate (3:1, 14 mL). The obtained crystals were dried under vacuum at room temperature for 18 hours, to give 1.40 g of white crystals. The crystals obtained in Example 7 were used as the seed crystals. The powder x-ray diffraction pattern for the obtained white crystals is shown in FIG. 7, and the typical peak values are shown in Table 8. The x-ray diffraction patterns were measured in the same manner as Example 12.

TABLE 8

| 2θ/θ values (°) of main peaks for white crystals |
|---|
| 6.6 |
| 7.2 |
| 8.8 |
| 14.6 |
| 15.8 |
| 16.4 |
| 17.6 |
| 18.7 |
| 20.9 |
| 22.1 |

Because the solid forms of formula (I) compound according to the present invention are uniform, have a high purity and are easy to work with as bulk medicaments for pharmaceutical manufacture, it is possible to industrially manufacture pharmaceuticals which contain formula (I) compound in a solid form as the active ingredient.

The invention claimed is:

1. A solid form of a compound (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide represented by formula (I):

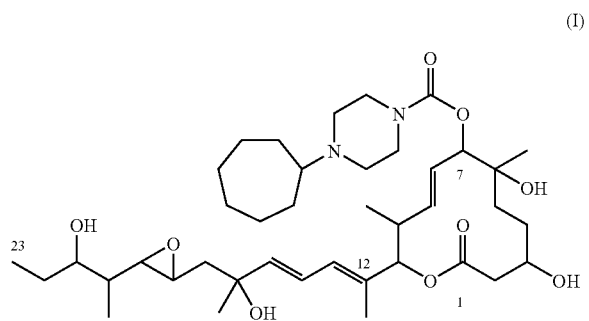

wherein the solid form is amorphous.

2. A solid form of a compound (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide represented by formula (I):

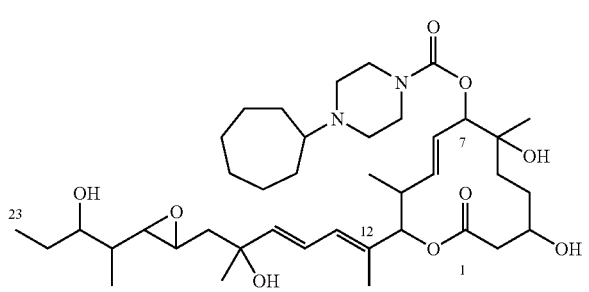

wherein the solid form is crystalline; and
wherein the crystals have, in a powder x-ray diffraction pattern thereof, peaks at the diffraction angles (2θ±0.2°) 8.8°, 15.8° and 17.5°.

3. A process for preparing the crystals of claim 2, comprising: dissolving the (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide in one or two solvents selected from the group consisting of a first ether-type solvent, aromatic hydrocarbon-type solvents, acetate ester-type solvents and alkylnitrile-type solvents to form a solution; then adding an aliphatic hydrocarbon-type solvent to the solution so as to induce crystal precipitation.

4. The process of claim 3, wherein the one or two solvents selected from the group consisting of a first ether-type solvent, aromatic hydrocarbon-type solvents, acetate ester-type solvents and alkylnitrile-type solvents are an acetate ester-type solvent.

5. The process of claim 3, wherein the acetate ester-type solvent is ethyl acetate.

6. The process of claim 3, wherein the aliphatic hydrocarbon-type solvent is n-heptane.

7. The process of claim 3, wherein crystal precipitation is induced under stirring.

8. The process for preparing the crystals of claim 3, wherein crystal precipitation is induced at 20 to 30° C.

9. The process for preparing the crystals of claim 3, wherein crystal precipitation is induced at 35 to 60° C.

10. The process for preparing the crystals of claim 3, wherein crystal precipitation is induced at 65 to 75° C.

11. The process of claim 3, wherein the (8E,12E,14E)-7-{(4-cycloheptylpiperazin-1-yl)carbonyl}oxy-3,6,16,21-tetrahydroxy-6,10,12,16,20-pentamethyl-18,19-epoxytricosa-8,12,14-trien-11-olide represented by formula (I) is prepared by the process comprising: reacting a compound represented by formula (VI):

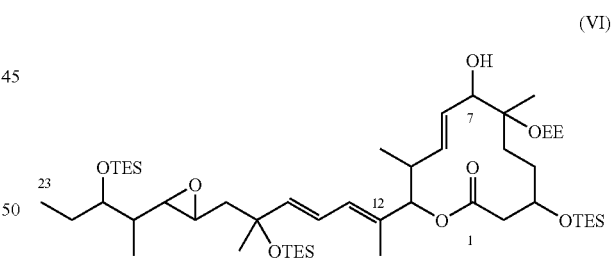

(wherein EE is 1-ethoxyethyl group, and TES is a triethylsilyl group) with a compound represented by formula (VII):

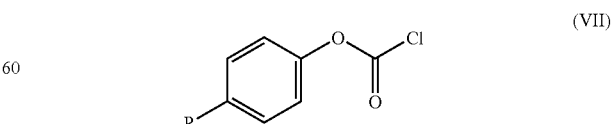

(wherein R is a nitro group, a chlorine atom or a hydrogen atom) using a second ether-type solvent so as to obtain an ether solution of the compound of formula (IV):

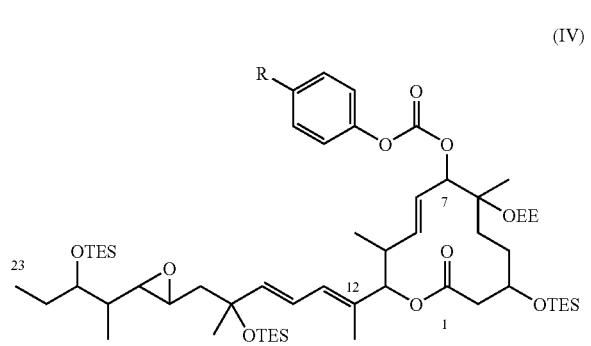

(IV)

(wherein EE, TES and R are as defined above); reacting the ether solution of the compound of formula (IV) with 1-cycloheptylpiperazine so as to form an ether solution of the compound represented by formula (III):

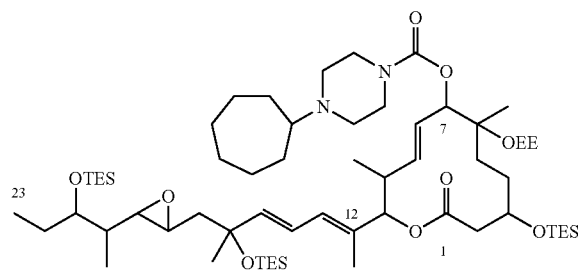

(III)

(wherein EE and TES are as defined above); treating the ether solution of the compound of formula (III) with a desilylating agent so as to deprotect the TES groups and thereby give an ether solution of the compound of formula (II):

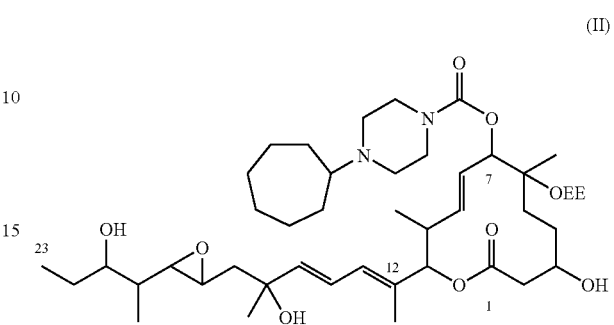

(II)

(wherein EE is as defined above); and treating the ether solution of the compound of formula (II) with an acid so as to deprotect the EE group.

12. The process of claim 11, wherein the second ether-type solvent is t-butyl methyl ether.

13. A pharmaceutical composition comprising the solid of claim 1 or 2.

* * * * *